US007917306B2

(12) United States Patent
Frumkin et al.

(10) Patent No.: US 7,917,306 B2
(45) Date of Patent: Mar. 29, 2011

(54) METHODS AND SYSTEMS FOR GENERATING CELL LINEAGE TREE OF MULTIPLE CELL SAMPLES

(75) Inventors: Dan Frumkin, Rechovot (IL); Adam Wasserstrom, Magshimim (IL); Shai Kaplan, Rechovot (IL); Uriel Feige, Rechovot (IL); Ehud Y. Shapiro, Nataf (IL)

(73) Assignee: Yeda Research and Developement Co. Ltd., Rehovot (IL)

( * ) Notice: Subject to any disclaimer, the term of this patent is extended or adjusted under 35 U.S.C. 154(b) by 848 days.

(21) Appl. No.: 11/887,551

(22) PCT Filed: Mar. 27, 2006

(86) PCT No.: PCT/IL2006/000385
§ 371 (c)(1),
(2), (4) Date: Oct. 1, 2007

(87) PCT Pub. No.: WO2006/103659
PCT Pub. Date: Oct. 5, 2006

(65) Prior Publication Data
US 2009/0292482 A1      Nov. 26, 2009

Related U.S. Application Data

(60) Provisional application No. 60/666,163, filed on Mar. 30, 2005.

(51) Int. Cl.
*C12P 1/00* (2006.01)
(52) U.S. Cl. .......................................... 702/20; 435/41
(58) Field of Classification Search ............... 702/20–24, 702/182–185, 188; 435/41
See application file for complete search history.

(56) References Cited

U.S. PATENT DOCUMENTS 5,639,600 A * 6/1997 McGrath et al. .................. 435/5
6,545,139 B1 * 4/2003 Thompson et al. .......... 536/23.5

OTHER PUBLICATIONS

International Preliminary Report on Patentability Dated Oct. 11, 2007 From the International Bureau of WIPO Re.: Application No. PCT/IL06/00385.
International Search Report Dated Jun. 15, 2007 From the International Searching Authority Re.: Application No. PCT/IL06/00385.
Invitation to Pay Additional Fees Dated Mar. 8, 2007 From the International Searching Authority Re.: Application No. PCT/IL06/00385.

(Continued)

*Primary Examiner* — Edward Raymond

(57) ABSTRACT

A method of generating a cell lineage tree of a plurality of cells of an individual is provided. The method comprising: (a) determining at least one genotypic marker for each cell of the plurality of cells; and (b) computationally clustering data representing the at least one genotypic marker to thereby generate the cell lineage tree of the plurality of cells of the individual.

7 Claims, 20 Drawing Sheets

OTHER PUBLICATIONS

Supplementary European Search Report and the European Search Opinion Dated Nov. 12, 2008 From the European Patent Office Re.: Application No. 06728189.9.

Written Opinion Dated Jun. 15, 2007 From the International Searching Authority Re.: Application No. PCT/IL06/00385.

Frumkin et al. "Genomic Variability Within An Organism Exposes Its Cell Lineage Tree", PLoS Computational Biology, XP002480067, 1(5): e50, Oct. 2005.

Kim et al "Methylation Reveals a Niche:Stem Cell Succession in Human colon Crypts", Oncogene (21): 5441-5449,2002. Morandi et al "Intraepidermal Cells of Paget's Carcinoma of the Breast Can Be Genetically Different From those of the Underlying Carcinoma", Human Pathology, 34 (12), 1321-1330, Dec. 12, 2003.

Office Action Dated Mar. 18, 2010 From the Israel Office Re.: Application No. 186084 and Its Translation Into English.

Response Dated Jul. 13, 2010 to Office Action of Mar. 18, 2010 From the Israel Office Re.: Application No. 186084.

Kluger et al. "Lineage Specificity of Gene Expression Patterns", Proc. Natl. Acad. Sci. USA, XP003016123, 101(17): 6508-6513, 2004.

Lu et al. "Expression of Bcl-2 in Bladder Neoplasms Is A Cell Lineage Associated and P53-Independent Event", Journal of Clinical Pathology: Molecular Pathology, 50: 28-33, 1997.

Braun et al. "ALES: Cell Lineage Analysis and Mapping of Developmental Events", Bioinformatics, 19(7): 851-858, 2003.

Di Rienzo et al. "Heterogeneity of Microsatellite Mutations Within and Between Loci, and Implications for Human Demographic Histories", Genetics, 148: 1269-1284, 1998.

Mehr et al. "Analysis of Mutational Lineage Trees From Sites of Primary and Secondary Ig Gene Diversification in Rabbits and Chickens", The Journal of Immunology, 172: 4790-4796, 2004.

Kluger et al. "Lineage Specificity of Gene Expression Patterns", Proc. Natl. Acad. Sci. USA, 101(17): 6508-6513, 2004.

* cited by examiner

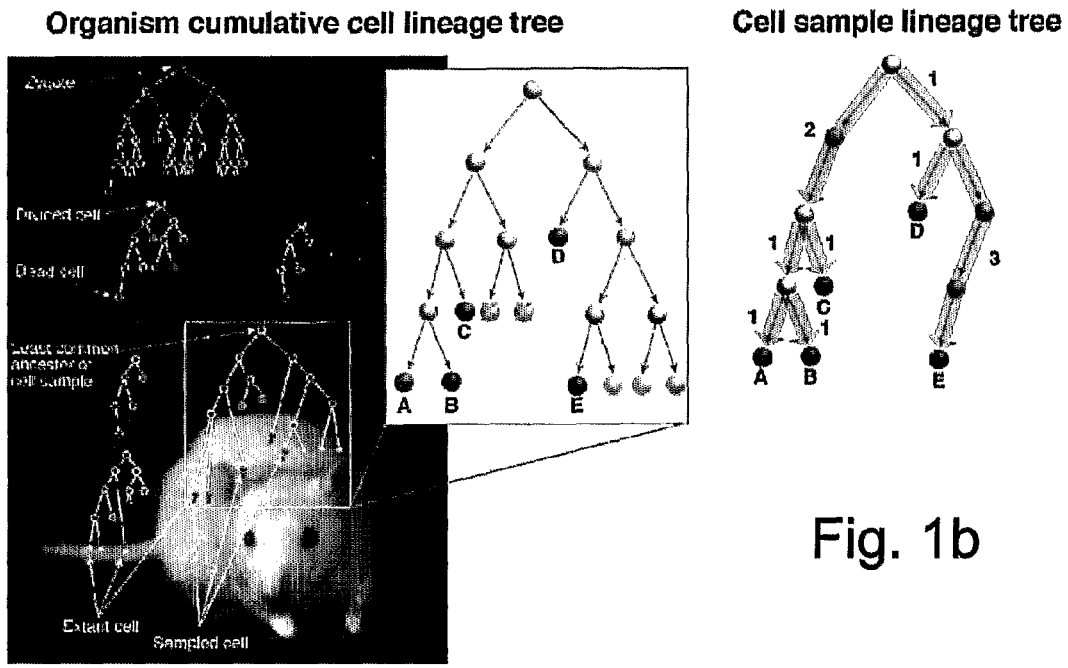
Fig. 1a
Fig. 1b
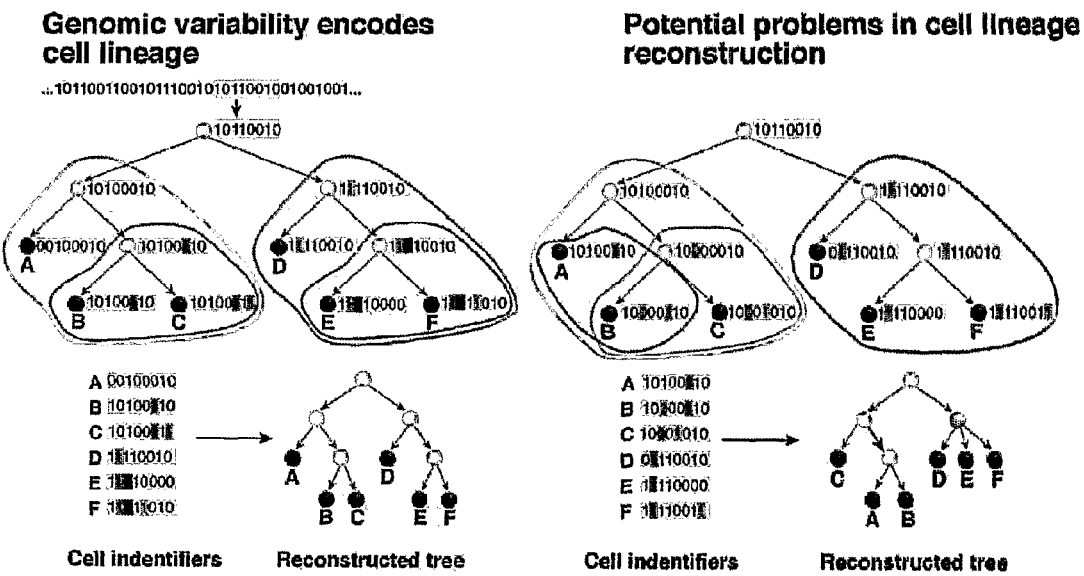
Fig. 1c
Fig. 1d

Single cells

Discrete cell clones

Fig. 5a
a Sampled *Arabidopsis* plant
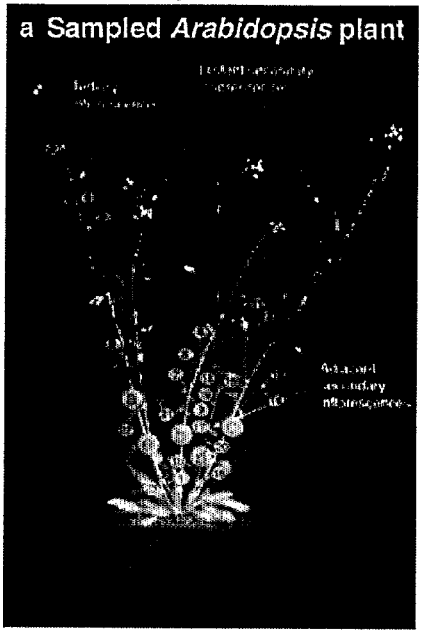
Fig. 5b
Transverse scheme of plant and samples
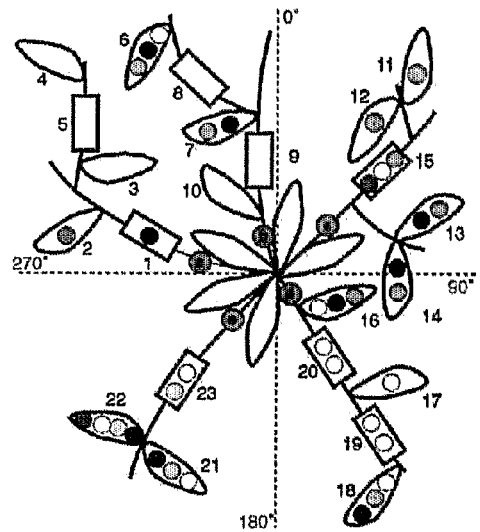
Fig. 5c
Sample identifiers
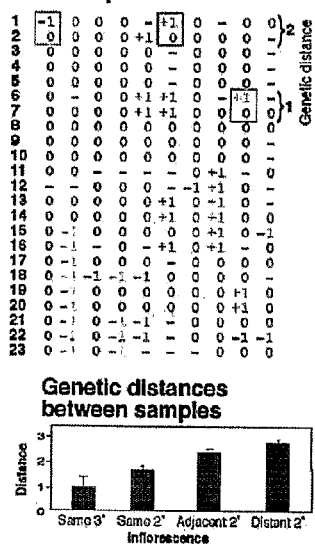
Genetic distances between samples
Fig. 5d
Fig. 5e
Sampled *Robinia pseudoacacia* tree
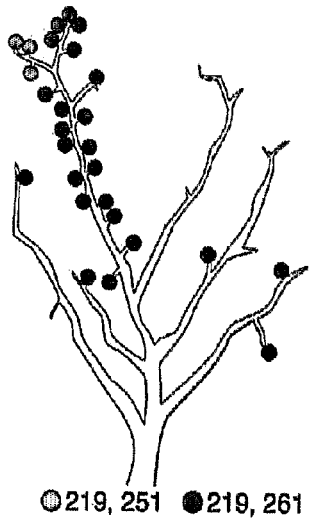

Zygote
Various tissue progenitors
Regular tissue
Primary tumor founder cell
Primary tumor
Metastasis founder cell
Metastasis
Metastasic cells

METHODS AND SYSTEMS FOR GENERATING CELL LINEAGE TREE OF MULTIPLE CELL SAMPLES

RELATED APPLICATIONS

This Application is a National Phase of PCT Patent Application No. PCT/IL2006/000385 having International Filing Date of Mar. 27, 2006, which claims the benefit of U.S. Provisional Patent Application No. 60/666,163 filed on Mar. 30, 2005. The contents of the above Applications are all incorporated herein by reference.

FIELD AND BACKGROUND OF THE INVENTION

The present invention relates to methods and systems for generating cell lineage tree of a multiple cell samples and, more particularly, which can be used for assessing clonality of a tumor.

A multicellular organism develops from a single cell, the zygote, through numerous binary cell divisions and cell deaths. Consequently, the lineage relations between the cells of the organism can be represented by a rooted labelled binary tree (FIG. 1a). Such a tree was reconstructed for the 959 somatic cells of *Caenorhabditis elegans* by direct observation (1). Understanding the cell lineage trees of higher organisms, especially Human, is a fundamental challenge of many branches of biology (2-10) and medicine (11-15). Development of higher organisms is, however, less deterministic than that of *C. elegans* and therefore the cell lineage trees of individuals of the same species may vary considerably.

Lineage relations among cells have been studied using a variety of clonal assays (2, 3, 6, 8, 10, 16-23). Such assays act by detecting the progeny of a single founder cell, which has been marked by a unique heritable marker. Some assays mark the founder cell by an invasive technique such as injection of a tracer molecule 16, 18 or retroviral infection 10, which may interfere with the normal growth and the biological function of the marked cell population.

Another approach is to detect the progeny of a founder cell that has been affected by a spontaneous mutation or an epigenetic change. Examples include loss or gain of large genomic fragments (19), mitochondrial DNA mutations (20), T cell receptor gene recombinations (21), X-chromosome inactivation (22), and changes in the number of MS repeat units (15, 23). A clonal assay provides limited lineage information because it only determines whether certain cells belong to the sub-tree of the organism cell lineage tree rooted by the clone founder. More subtle lineage relations have been uncovered using quantitative analysis of multiple somatic mutations, enabling the estimation of tumour age and the reconstruction of human tissue lineage trees. In one study (24), tissue samples from breast cancer patients were analyzed for loss of heterozygosity and mutations in mitochondrial DNA, and the result of this analysis was fed into a phylogenetic algorithm, yielding tissue lineage trees. In a different study (25), mismatch repair (26, MMR) deficient colorectal cancer and adenoma tissue samples (which display MS instability) were analyzed for mutations in MS loci. Tissue samples were assigned genotypes from the modes of their MS allele length distributions, and the genotypes were analyzed according to a model of tumour development, yielding reconstructed lineage trees. These studies have tried to exhibit that in certain tissues, lineage trees can be reconstructed from genomic variability.

It should be noted, however, that the above-described lineage analyses were all effected on heterogeneous tissue samples in which lineage relations are undefined and cannot be represented by a binary tree.

There is thus a widely recognised need for and it would be highly advantageous to have methods of identifying cell-lineage tree which are devoid of the above-limitations.

SUMMARY OF THE INVENTION

According to one aspect of the present invention there is provided a method of generating a cell lineage tree of a plurality of cells of an individual, the method comprising: (a) determining at least one genotypic marker for each cell of the plurality of cells; and (b) computationally clustering data representing the at least one genotypic marker to thereby generate the cell lineage tree of the plurality of cells of the individual.

According to another aspect of the present invention there is provided a method of assessing clonality of a neoplasm in an individual, the method comprising: (a) obtaining a cell sample of the neoplasm of the individual; (b) determining at least one genotypic marker for each cell of the cell sample of the neoplasm; and (c) computationally clustering data representing the at least one genotypic marker and additional genotypic markers of a plurality of cells, to thereby assess clonality of the neoplasm in the individual.

According to further features in preferred embodiments of the invention described below, the neoplasm is of a blood forming tissue.

According to still further features in the described preferred embodiments the plurality of cells are from healthy tissues, tumor tissues or a combination thereof.

According to still further features in the described preferred embodiments the neoplasm is a cancer of unknown primary tumor.

According to yet another aspect of the present invention there is provided a method of identifying presence of tumor stem cells, the method comprising: (a) determining at least one genotypic marker for each cell of a cell sample of a tumor; (b) computationally clustering data representing the at least one genotypic marker to thereby generate a cell lineage tree of the tumor; and (c) mapping cells in the cell lineage tree, thereby identifying the presence of tumor stem cells.

According to still another aspect of the present invention there is provided a system for generating a cell-lineage tree of a plurality of cells, the system comprising a processing unit, the processing unit executing a software application configured for: (i) determining at least one genotypic marker for each cell of the plurality of cells; and (ii) clustering data representing the at least one genotypic marker and producing a cell-lineage tree of the plurality of cells.

According to still further features in the described preferred embodiments the genotypic marker is a cell division marker.

According to still further features in the described preferred embodiments the genotypic marker exhibits somatic variability.

According to still further features in the described preferred embodiments the genotypic marker exhibiting somatic variability is a repetitive sequence element.

According to still further features in the described preferred embodiments the repetitive sequence element is a microsatellite.

According to still further features in the described preferred embodiments the clustering is effected by a clustering algorithm.

According to still further features in the described preferred embodiments the clustering algorithm is selected from the group consisting of Maximum parsimony, Distance matrix-based algorithms and Maximum likelihood.

According to still further features in the described preferred embodiments the system further comprises a programmable laboratory robot for obtaining the at least one genotypic marker.

According to still further features in the described preferred embodiments the programmable laboratory robot comprises a PCR machine and an electrophoresis apparatus.

According to still further features in the described preferred embodiments the programmable laboratory robot comprises a PCR machine and a signal detection apparatus.

According to still further features in the described preferred embodiments the programmable laboratory robot comprises a PCR machine and a mass spectroscopy apparatus.

According to an additional aspect of the present invention there is provided a method of assessing growth dynamics of a population of cells of interest, the method comprising determining cell depth of at least two samples of the population of cells of interest, each of the two samples being of a different age, thereby assessing growth dynamics of the population of cells of interest.

According to still further features in the described preferred embodiments the population of cells comprises a population of neuronal cells.

According to still further features in the described preferred embodiments the population of cells comprises a population of stem cells.

According to still further features in the described preferred embodiments the age refers to a period of time from zygote fertilization.

According to still further features in the described preferred embodiments the age refers to a period of time from culture establishment.

The present invention successfully addresses the shortcomings of the presently known configurations by providing methods and systems for generating a cell lineage tree of a plurality of cells.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1a-g are annotated diagrams describing various concepts in cell lineage: FIG. 1a shows how multicellular organism development can be represented by a rooted labeled binary tree called the organism cumulative cell lineage tree. Nodes (circles) represent cells (dead cells are crossed) and each edge (line) connects a parent with a daughter. The uncrossed leaves, marked blue, represent extant cells; FIG. 1b shows how any cell sample (A-E) induces a sub-tree, which can be condensed by removing non-branching internal nodes, and labeling the edges with the number of cell divisions between the remaining nodes. The resulting tree is called the cell sample lineage tree. The tree is said to be geometrical if it includes the edge labels and topological if the edge labels are removed; FIG. 1c shows how the genome of a hypothetical organism consists of a string of binary digits and accumulates mutations in the form of bit flips (colored). In this example lineage analysis utilizes a representation of a small fraction of the genome (eight bits), called the cell identifier. Phylogenetic analysis reconstructs the tree from the cell identifiers of the sample. If the topology of the cell sample lineage tree is known, reconstruction can be scored; FIG. 1d shows how colliding mutations, namely two or more identical mutations that occur independently in different cell divisions (A, B), and silent cell divisions, namely cell divisions in which no mutation occurs (D-F), may result in incorrect (red edge) or incomplete (unresolved ternary red node) lineage trees.

FIG. 1a shows that microsatellites are DNA segments comprised of a short sequence repeated several times. PCR of an MS locus from a DNA sample followed by capillary electrophoresis yields a histogram which is compared to a reference histogram yielding the relative allelic values of the sample at this locus; FIG. 2b shows that two types of random geometrical trees with 32 leaves were generated and MS stepwise mutations were simulated. Results of simulations of wild-type human using different numbers of MS loci are shown. The white line states the perfect score limit (according to the Penny & Hendy tree comparison algorithm[28]). The results show that it is possible to accurately reconstruct the correct tree for trees of depth equivalent to human newborn and mouse newborn (marked by blue and green dots respectively) using the entire set of MS loci. A mathematical analysis (also marked by green dot) proves that any tree of depth 40 can be reconstructed with no errors. Simulations with MS mutation rates of MMR-deficient organisms demonstrate that cell lineage reconstruction is possible with no more than 800 MS loci (the white line states the 0.95 score). The quality of reconstruction depends on the topology of the tree and its maximal depth that together influence the signal to noise ratio.

FIG. 4a shows how a cell sample lineage tree with a pre-designed topology is created by performing single-cell bottlenecks on all the nodes of the tree. Lineage analysis is performed on clones of the root and leaf cells. Three TCTs (A-C) were created using LS174T cells which display MS instability; FIG. 4b shows the tree structure of TCT A (black nodes and edges). The reconstructed tree is shown in the inset; FIG. 4c shows the tree structure of TCT B (black nodes and edges). The reconstructed tree is shown in the inset; FIG. 4c shows the tree structure of TCT C (black nodes and edges). The reconstructed tree is shown in the inset. For FIGS. 4b-d, all topologies were reconstructed precisely. Edge lengths were drawn in proportion to the output of the algorithm. Gray edges represent correct partitions according to the Penny & Hendy tree comparison algorithm[28], and their width represents the bootstrap value[28] (n=1000) of the edge. A minimal set of loci yielding perfect reconstruction was found for each TCT. Each colored contour represents a different mutation shared by the encircled nodes; FIG. 4e is a graph showing the relationship between the average reconstruction scores of TCTs A-C and random subsets of MS loci of increasing sizes (average over 500); FIG. 4f is a graph showing the linear correlation ($R^2$=0.955) between reconstructed and actual node depths.

FIGS. 5a-e exemplify lineage analysis of a plant; FIG. 5a is a photograph of the *Arabidopsis thaliana* plant used for the experiment. Samples from the same tertiary inflorescence are considered to be physically closest, followed by samples from the same secondary (but not tertiary) inflorescence, samples from adjacent inflorescences, and samples from distant inflorescences; FIG. 5b is an annotated diagram of a transverse scheme of the plant showing all sampled stem (rectangles) and cauline leaf (ovals) tissues. Mutations which occurred in two or more samples are depicted by coloured circles; FIG. 5c is a chart of an example of the sample identifiers obtained, including all loci in which mutations occurred. Coloured mutations correspond to circles in the scheme. Hyphens represent un-amplified loci. The genetic distance between loci is the sum of loci with different values; FIG. 5d is a bar graph showing how the genetic distance between two samples increases with increasing physical-radial distance; FIG. 5e is a photograph and scheme of the *Robinia pseudoacacia* tree used for the lineage experiment. All three mutated samples come from the same small branch.

FIG. 6 is a table showing the full set of identifiers obtained for TCT A, TCT B and TCT C.

FIG. 11a depict assumed sequence of events, wherein a primary tumor originates from a single cell in one of the tissues (red) and after some clonal expansion, a metastasis originates from a single cell from the primary tumor. FIG. 11b—identification of the tissue of origin is performed by taking samples the cancerous tissue and from potential tissues of origin. The identifier of metastatic cells is expected to be closer to cells of the tissue of origin of the metastasis.

DESCRIPTION OF THE PREFERRED EMBODIMENTS

Figure 1E:
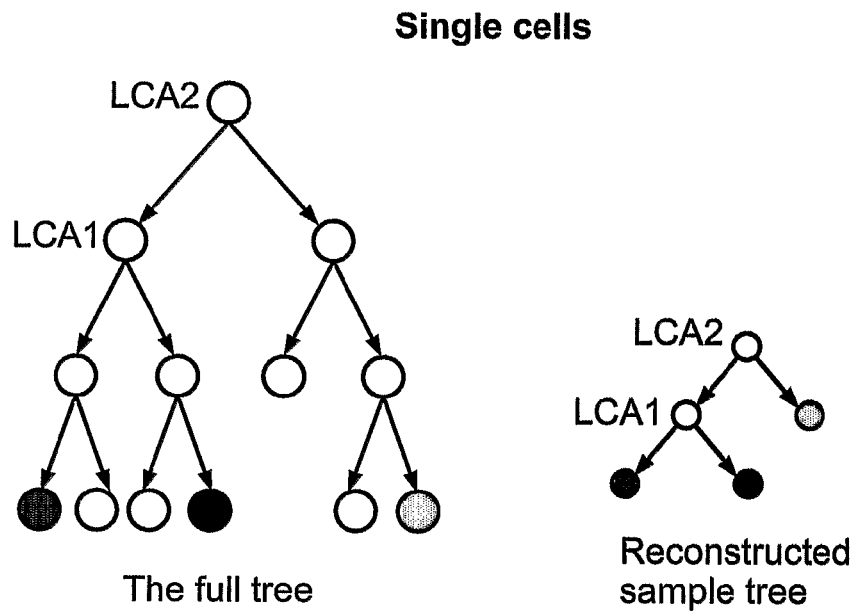

The present invention is of methods of generating cell lineage trees which can be used in the fields of developmental biology, immunology and cancer research, such as for assessing clonality of tumors.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The study of cell lineages has been, and remains, of crucial importance in developmental biology, immunology, stem-cell research, brain research, and cancer research, yet complete cell lineage trees were reconstructed only for simple organisms such as the nematode *C. elegans*.

Various approaches for elucidating cell lineages are known in the art [see review by Stern and Fraser (2001) Nature Cell Biol. 3:E216]. For example, direct observation which has been historically used for tracing the complete lineage of *C. elegans*. However, this approach is limited by the ability of the observer to identify a single cell and all its descendents unambiguously at successive times, which is not always possible, even with time lapse cinematography. Other approaches include the use of vital dyes and radioactively labeled compounds, however these approaches are limited by non-specificity and the technical obstacle of applying to single cells. Other methods of using exogenous markers for studying single cell lineages are technically difficult to pursue and limited by the dilution of the marker with cell divisions. This should be of special concern when studying rapidly dividing cells. The use of exogenous genetic markers such as retroviral vectors encoding a marker is limited by the possibility that the virus interfere with cell division, reflecting thereby on the lineage.

The use of endogenous genetic markers for tracing cell lineage has been described especially with respect to assessing clonality of tumor cells [24, 41]. Briefly, DNA from different tissue sections (each including hundreds of cells) was compared using a mathematical algorithm [e.g., neighbour joining (NJ) algorithm], which outputted a binary lineage tree. However, since analysis is performed at the tissue level, the resultant binary trees cannot be considered valid, as lineage relations at the tissue level are undefined.

While reducing the present invention to practice, the present inventors uncovered that lineage analysis performed on single cells or clones thereof using an endogenous genetic marker can be used to reconstruct cell lineage tree of a tissue or even of an entire individual.

Thus, according to one aspect of the present invention there is provided a method of generating (i.e., elucidating) a cell lineage tree of a plurality of cells of an individual. The method comprising: determining at least one genotypic marker for each cell of the plurality of cells; and computationally clustering data representing the at least one genotypic marker to thereby generate the cell lineage tree of the plurality of cells of the individual.

As used herein the phrase "cell lineage tree" refers to the developmental relationships between cells, identifying cells with common ancestry and cells which are developmentally close to each other. The cell lineage tree of the present invention can be graphically presented as a tree as further described hereinbelow.

As used herein the phrase "plurality of cells" refers to a plurality of single cells or to a plurality of clones of single cells. If a plurality of single cells are used by the present invention, then the genotypic marker is determined in each of these cells. If a plurality of clones of single cells are used, then the genotypic marker can be determined on pools of DNA extracted from these clones, as further described hereinbelow and in the Examples section which follows.

As used herein the term "individual" refers to a multicellular organism, such as a plant, a fungus or an animal such as a vertebrate or an invertebrate.

As used herein the phrase "genotypic marker" refers to a genetic or an epigenetic element which provides sufficient information, such as somatic variability, to reconstruct the cell lineage tree of the present invention. The genotypic marker of the present invention can be a genomic subsequence, or optionally include the entire genome of the individual. The genotypic marker of the present invention may be randomly mutated genotypic marker or a marker which mutates in correlation with cell division (i.e., directional marker, cell division marker), hence is informative of a number of cell divisions.

Somatic variability results from somatic mutations, which may include a number of different types of alterations in DNA structure, including deletions, translocations and single nucleotide alterations. Somatic mutations may occur spontaneously as a result of mistakes in DNA replication or be induced by environmental factors. In addition, the RNA editing process, in which the coding sequence of the transcript is altered from its genomic version, can also be a source of somatic hypermutations.

Examples of genetic elements which can be used in accordance with the present invention include, but are not limited to, repetitive sequence elements, such as of the Alu and L1 family of sequences in humans and the satellite, minisatellite and microsatellite sequences (MS). As is illustrated in Example 1 of the Examples section which follows, the present inventors have demonstrated through laborious calculations that MS mutations provide sufficient information for lineage tree reconstruction, as evidenced by the quality of tree reconstruction based on such information. An example of a directional marker is telomerase which shortens concomitantly with cell divisions.

Examples of epigenetic elements which can be used in accordance with the present invention include, but are not limited to, DNA methylation. Methods of determining DNA methylation are well known in the art, including restriction enzyme digestion-based methylation detection and bisulphate-based methylation detection. Further details on techniques useful for detecting methylation are disclosed in Ahrendt (1999) J. Natl. Cancer Inst. 91:332-9; Belinsky (1998) Proc. Natl. Acad. Sci. USA 95:11891-96; Clark (1994) Nucleic Acids Res. 22:2990-7; Herman (1996) Proc. Natl. Acad. Sci. USA 93:9821-26; Xiong and Laird (1997) Nuc. Acids Res. 25:2532-2534].

A combination of randomly mutated markers and directional markers may be preferably employed to infer accurate cell lineage, according to this aspect of the present invention.

The genotypic marker of this aspect of the present invention is selected to provide enough information to reconstruct the cell lineage tree of the present invention, even in the presence of colliding mutations (two or more identical mutations that occur independently in different cell divisions) or silent cell divisions. (i.e., cell divisions in which no mutation occurs). For further description, see Example 1 of the Examples section which follows.

As mentioned the genotypic marker of the present invention can be determined for each cell of the plurality of cells. When single cell samples are used advanced material collection methods are used and single cell genetic analysis is performed. This may be effected by single-cell PCR, whole genome amplification (WGA) procedures, single-cell complementary DNA arrays and even single-cell comparative genomic hybridization. See for example, Kuppers Cancer Surv. 1997; 30:45-58; Hahn et al. Cell Mol Life Sci. 2000 Jan. 20; 57(1):96-105]. In situ PCR and in situ RT-PCR are known in the art as means to detect nucleic acid sequences in single cells (U.S. Pat. No. 5,436,144).

For example, when lineage analysis is performed on single cells, DNA enrichment is achieved by WGA allowing subsequent multiple PCR reactions in parallel, which are practically unlimited in number. WGA can be effected using any method known in the art such as, MDA—multiple displacement amplification, and PEP—primer extension pre-amplification [Hellani et al. Mol. Hum. Reprod.2004; 10: 847-852].

For example, a biological sample comprising a plurality of cells can be a resuspended in buffer and cytospun onto a slide. Using a light microscope and a micromanipulator, single cells can be picked with a drawn glass capillary and placed in PCR microfuge for single cell PCR amplification. The cellular proteins are first digested in for example, SDS/proteinase K for 1 hour, followed by heating to 99° C. for 30 minutes to denature the proteinase K and to further denature and expose the chromosomal DNA. Standard or nested PCR can be then performed such as described in Example 3 of the Examples section. Single cell PCR is typically effected under long denaturing conditions (95° C. for 10 minutes), cooling down (spin the tray down before opening the caps) and addition of PCR reaction mixture (e.g., primers, buffer, polymerase and dNTPS). A preceding step of WGA may be effected prior to PCR amplification of the genotypic markers.

Alternatively, single cells can be isolated and grown to obtain isolated clones thereof. In this case, each single cell is isolated from a biological sample, allowed to is proliferate for a desired number of cell divisions (e.g., $1 \cdot 10^6$ cells) and genotypic analysis is performed on DNA samples obtained from these cell clones. It should be noted that using DNA sampled from cell clones instead of directly from single cells is not expected to affect analysis results.

Regardless of the procedure employed, once genetic material is at hand, determination of the genotypic marker can be effected using any sequencing method known in the art. These include direct and indirect DNA sequencing methods. Direct DNA sequencing refers to base-by-base analysis, with each new base determination built on the results of many previous sequencing steps. Such an approach is preferably used when short genotypic markers are under examination (e.g., shorter than 1000 bases) to maintain accuracy. Direct sequencing techniques involve a variety of synthesis, degradation or separation techniques and include the traditional Sanger, pyrosequencing and exonuclease methods, as well as direct visualization approaches [Sanger (1977) Proc. Natl. Acad. Sci. USA 74:5463; Hyman (1988) Anal. Biochem. 158:423; Ronaghi (2001) Genome Res. 11:3; Jett (1989) J. Biomol. Struct. Dyn. 7:301; Lindsay (1991) Genet. Anal.

Tech. Appl. 8:8; Beebe (1989) Science 243: 370; Woolley (2000) Nat. Biotechnol. 18:760; Church (1998) U.S. Pat. No. 5,795,782].

In the Sanger method, DNA synthesis is randomly terminated at each base pair, creating a wide range of fragments that are then separated by gel according to length and scored. In the pyrosequencing method, polymerase-guided incorporation of each base is detected by measuring the pyrophosphate released in consecutive cycles, In the exonuclease approach, a single molecule of target DNA synthesized with fluorescent-tagged bases is degraded by exonuclease. The consecutively released nucleotides are then scored with a sensitive fluorescence detector. Another class of direct sequencing methods relies on base visualization, using either scanning-tunneling microscopy or nano-pores.

Indirect sequencing methods, such as sequencing by hybridization, are based on determining the oligonucleotide content of the target nucleic acid and do not require determination of base position information experimentally. Oligonucleotide content may be obtained by fragmenting the DNA and separating the resulting oligonucleotides based on physiochemical properties, or by hybridization of oligonucleotides to complementary sequences present in the test DNA. The complete sequence is then determined by compiling the results of many such tests.

Another method of determining nucleic acid sequences depends on mass spectroscopy (MS). As is known to one of ordinary skill in the art, identification of nucleotide sequences of nucleic acid fragments by MS depends on mass determination of the nucleic acid fragments with sufficient accuracy so that each base can be recognized by its unique mass. See, e.g., Fitzgerald et al., Rapid Commun. Mass Spectrom. 7: 895-897 (1993). A mass accuracy achieved has been reported to be typically better than 0.1%. See, e.g., Bentley et al., Anal. Chem. 68:2141-2146 (1996). MS methods of improved resolution and sensitivity and applicable to complex mixtures of oligonucleotides have been developed. These are based on a variation of the matrix-assisted laser desorption/ionization time of flight method (MALDI-TOF) using delayed ion extraction (DE-MALDI). See, e.g., Roskey et al., Proc. Natl. Acad. Sci. USA 93:4724-4729 (1996), which reports that by coupling a high yield cycle sequencing protocol to DE-MALDI, sequencing of dideoxy-terminated DNA mixtures of templates up to 40 or 50 bases long was achieved.

Genotypic data obtained as described herein is then clustered to thereby generate the cell lineage tree of the plurality of cells of the individual. Genotypic data can be clustered as is, or can be encoded to a coded representation of the genotypic marker (i.e., identifier) and then clustered.

Computational clustering can be effected using clustering algorithms, such as phylogenetic algorithms. Phylogenetics is the scientific discipline concerned with describing and reconstructing the patterns of genetic relationships among species and among higher taxa. Phylogenetic trees are a convenient way of visually representing the evolutionary history of life. These diagrams illustrate the inferred relationships between organisms and the order of speciation events that led from earlier common ancestors to their diversified descendants. As such phylogenetic algorithms can be used to reconstruct the lineage trees of the present invention. In general, a phylogenetic tree has several parts. Nodes typically represent taxonomic units, such as a population of cells and a common ancestor. Branches connect nodes uniquely and represent genetic relationships. The specific pattern of branching determines the tree's topology. Scaled trees have branch lengths that are proportional to some important biological property, such as the number of cell divisions between nodes. Trees may also be rooted or unrooted. Rooted trees have a special node, known as the root, that represents a common ancestor of all taxa shown in the tree. Rooted trees are thus directional, since all taxa evolved from the root. Unrooted trees illustrate relationships only, without reference to common ancestors.

Several algorithmic methods have been devised to infer correct phylogenetic trees. The following outlines some of the methods which can be used in accordance with the present invention. Each method can be used to infer a lineage tree from genotypic data obtained as described herein.

Maximum parsimony—One of the oldest, most basic, and most frequently used methods for character (An observable feature of a cell distinguishing it from another. i.e., genotypic marker) resolution is the maximum parsimony (MP) criterion (Edwards, A. W. F. and Cavalli-Sforza, L. L. (1963) "The reconstruction of evolution." Annals of Human Genetics 27: 105-106; Kitching, I. J., Forey, P. L., Humphries, C. J., and Williams, D. M. (1998) Cladistics: The Theory and Practice of Parsimony Analysis. Second Edition. The Systematics Association Publication No. 11. Oxford: Oxford University Press]. The parsimony criterion mandates that the best tree describing the data is the tree that minimizes the amount of character conflict. Currently, parsimony is the method of choice for reconstructing morphological trees [Kitching et al. (1998), supra]. It is very fast computationally, and it can be robust to differences in evolutionary rate among characters. However, maximum parsimony consistently finds the correct phylogeny only when we expect character conflict to be low or evolution to proceed parsimoniously [Felsenstein, J. (2004) Inferring Phylogenies. Sunderland, Mass.: Sinauer Associates]. If rates of evolution are slow and branches are short, character conflict will be low and parsimony will work well. If character conflict is moderate or high in reality, then it is very unlikely that the true tree will have the least amount of character conflict. When rates of evolution are high, or when some branches are very long, or when the number of possible character states is limited, character conflict can be common. This is often true for nucleotide sequences, which have only four possible character states (A, C, T, or G). In cases such as these, other phylogenetic methods can be more accurate than parsimony.

Maximum likelihood—Another commonly used phylogenetic criterion is maximum likelihood (ML), an effective and robust statistical technique now used in all scientific fields [Edwards, A. W. F. and Cavalli-Sforza, L. L. (1964) "Reconstruction of phylogenetic trees." in Phenetic and Phylogenetic Classification. ed. Heywood, V. H. and McNeill. London: Systematics Assoc. Pub No. 6; Felsenstein, J. (1981) "Evolutionary trees from DNA sequences: A maximum likelihood approach." J Mol Evol 17: 368-376; Fisher, R. A. (1912) "On an absolute criterion for fitting frequency curves." Messenger of Mathematics 41: 155-160]. Many well-known statistical estimators are actually maximum likelihood estimators. For example, the common sample average as an estimate of the mean of a Gaussian distribution and the least-squares fit of a line to a set of points are both maximum likelihood estimators. Using ML, one can infer rates of evolution directly from the data and determine the tree that best describes that data given those inferred rates. In other words, ML finds the tree and evolutionary parameters that maximize the probability of the observed data. Unlike parsimony, ML finds trees with the expected amount of character conflict given the evolutionary rates inferred from the data, even if those rates are high. ML is a computationally intensive method that can be very time-consuming.

Distance methods—Due to their computational speed, distance matrix methods are some of the most popular for inferring phylogenies [Nei, M. and Kumar, S. (2000) Molecular Evolution and Phylogenetics. New York, N.Y.: Oxford University Press]. All distance methods transform character data into a matrix of pairwise distances, one distance for each possible pairing of the taxa under study. Distance matrix methods are not cladistic (A class of phylogenetic techniques that construct trees by grouping taxa into nested hierarchies according to shared derived characters), since the information about derived and primitive characters has been lost during this transformation. Distance methods approach phylogenetic inference strictly as a statistical problem, and they are used almost exclusively with molecular data. Although they are not cladistic, distance methods can be thought of as approximations to cladistic methods, and several of the methods are guaranteed mathematically to converge on the correct tree as more data is included. The most simple distance metric is merely the number of character differences between two taxa, such as the number of nucleotide differences between two DNA sequences. Many other ways of calculating molecular sequence distances exist, and most attempt to correct for the possibility of multiple changes at a single site during evolution. Methods for calculating distances between sequences are usually named for their originators, such as Kimura's two-parameter (K2P), Jukes-Cantor (JC), Tamura-Nei (TN), Hasegawa, Kishino, and Yano (HKY), and Felsenstein 1984 (F84). Other important distance metrics are General Time Reversible (GTR) and LogDet.

Once a distance matrix for the taxa being considered is in hand, there are several distance-based criteria and algorithms that may be used to estimate the phylogenetic tree from the data). The minimum evolution (ME) criterion finds the tree in which the sum of all the branch lengths is the smallest. Weighted and unweighted least squares criteria calculate the discrepancy between the observed pairwise distances and the pairwise distances calculated from the branch lengths of the inferred tree. Least squares then finds the tree that minimizes the square of that discrepancy. Least squares methods are some of the most statistically justified and will converge on the correct tree as more data are included in the analysis (given a mathematically proper distance metric). The neighbor-joining (NJ) algorithm is extremely fast and is an approximation of the least squares and minimum evolution methods. If the distance matrix is an exact description of the true tree, then neighbor-joining is guaranteed to reconstruct the correct tree. The UPGMA clustering algorithm (a confusing acronym) is also extremely fast, but it is based upon the unlikely assumption that evolutionary rates are equal in all lineages. UPGMA is rarely used today except as an instructional tool.

Using either of the above described clustering algorithms a cell lineage tree of a plurality of cells or even of an entire individual can be reconstructed.

It will be appreciated that the resultant tree may be used to obtain depth information from the topology and edge length. Basically, the distance between two nodes u,v is the number of edges in the path with endpoints u and v. The depth of a node u is its distance from r (the root of the tree). As such, the distance between any two cells, specifically the depth of any cell (its distance from the root of the tree) can be inferred.

The methods of the present invention are preferably carried out using a dedicated computational system.

Figure 10:
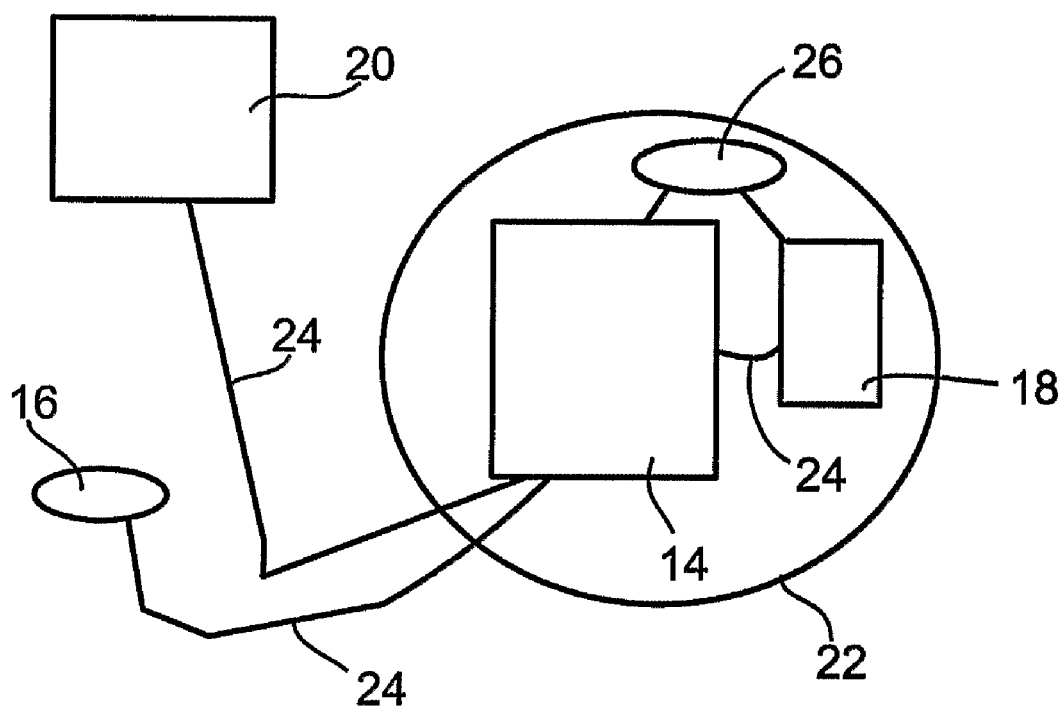
FIG. 10 is a schematic illustration showing one configuration of the system of the present invention.

Thus, according to another aspect of the present invention and as illustrated in FIG. 10, there is provided a system for generating cell lineage tree of a plurality of cells of an individual which system is referred to hereinunder as system 10 (see also Example 2 of the Examples section).

System 10 of this aspect of the present invention comprises a processor 14 for determining at least one genotypic marker for each cell of the plurality of cells; and clustering data representing the at least one genotypic marker and producing a cell-lineage tree of the plurality of cells.

Processor 14 may be included in any computing platform 22 known in the art including but not limited to, a personal computer, a work station, a mainframe and the like.

Computing platform 22 may also include a user input interface 16 (e.g., a keyboard and/or a mouse) for inputting data (i.e., genotypic markers) or querying data, and a user output interface 18 (e.g., a monitor, a printer) for providing lineage information to a user.

Alternatively, genotypic data is generated by a programmable laboratory robot 20 which is connected to processor 14. Laboratory robot 20 is configured for collecting DNA samples, amplifying DNA by PCR, and/or sequencing a selected genotypic marker in a partly or wholly automatic manner. Hence laboratory robot may comprise for example, a PCR machine and an electrophoresis apparatus for direct DNA sequencing, a PCR machine and a fluorescence detection apparatus for hybridization based sequencing or a PCR machine and a mass spectrometry apparatus, for mass-spectrometry based sequencing. Laboratory robots can be commercially obtained such as from Life Science Automation http://www.ssirobotics.com/Life-Sciences.html.

System 10 preferably stores lineage information generated thereby on a computer readable medium 26 such as a magnetic, optico-magnetic or optical disk.

Cell lineage analysis effected according to the teachings of the present invention can be used in numerous applications, such as in the fields of developmental biology, neurobiology, cancer and immunology.

For example, the teachings of the present invention can be used to assess a clonality of a neoplasm. As used herein the term "neoplasm" refers to an abnormal growth of a tissue which may be benign or malignant, such as, for example, the malignant neoplasm of blood forming tissue.

As used herein the term "clonality" refers to the cell origin of a neoplasm. Essentially determining if a given neoplasm is a result of a primary tumor cell migration or a result of a synchronous independent neoplastic transformation; Alternatively determining tissue identity of a primary tumor.

Determination of tumor clonality is highly important to cancer research, diagnosis and therapy.

For example, Hodgkin's lymphoma (HL) is characterized by typical mononucleated Hodgkin and multinucleated Reed-Sternberg cells, which occur at low frequency in a mixed cellular infiltrate in the tumor tissue. Because of the rarity of these cells and their unusual immunophenotype, which is strikingly different from those of all normal hematopoietic cell types, the origin of these cells and their clonality have long been unclear [Kuppers Adv Cancer Res. 2002; 84:277-312].

Another example, is the multifocal occurrence and frequent recurrence which feature urothelial carcinomas of both the urinary bladder and the upper urinary tract. To describe the clonal nature of these tumors, two theories have been proposed. The monoclonality hypothesis describes the multiple tumors as descendants of a single genetically transformed cell spreading throughout the urothelium. In contrast, field cancerization caused by carcinogen exposure of the urothelium may lead to independent development of synchronous or metachronous nonrelated tumors at different sites of the urothelial tract. In the last 10 years, a multitude of molecular genetic studies have investigated the clonality of multifocal urothelial carcinomas, however to date the clonality of urothelial carcinomas is still enigmatic [Hafner C, Knuechel R, Stoehr R, Hartmann A. Int J Cancer. 2002 Sep. 1; 101(1): 1-6].

Thus, according to yet another aspect of the present invention there is provided a method of assessing clonality of a neoplasm in an individual. The method comprising obtaining a cell sample of the neoplasm of the individual; determining at least one genotypic marker for each cell of the cell sample of the neoplasm; and computationally clustering data representing the at least one genotypic marker and additional genotypic markers of a plurality of cells, to thereby assess clonality of the neoplasm in the individual.

Cell samples of neoplasms can be obtained by any biopsy procedure known in the art, such as fine needle biopsy, surgical biopsy and the like. Selection of the biopsy procedure primarily depends on the examined neoplasm.

Cells of the plurality of cells of this aspect of the present invention may include cells of benign or malignant neoplasms which are found in the individual. Alternatively or additionally, such cells can be obtained from healthy tissues.

It will be appreciated that once a clonality of a neoplasm is known, treatment regimen may be better suited to combat the disease. For example, treating of metastatic lesions of colon cancer characterized by high surface levels of TAG-72 antigen can be effected using monoclonal antibody $^{131}$I-CC49 [Kostakoglu Cancer Invest. 1994; 12(6):551-8].

The present invention may also be used to determine presence of tumor stem cells. While the majority of the cancer cells have a limited ability to divide, a population of cancer stem cells that has the exclusive ability to proliferate and form new tumors may exist and can be identified based on the teachings of the present invention.

Thus, according to still another aspect of the present invention there is provided a method of identifying presence of tumor stem cells. The method comprising: determining at least one genotypic marker for each cell of a cell sample of a tumor; computationally clustering data representing the at least one genotypic marker to thereby generate a cell lineage tree of the tumor; and mapping cells in the cell lineage tree, thereby identifying the presence of tumor stem cells. Essentially, a tumor which is characterized by a string like tree-topology is suspected of including tumor stem cells (cells mapped to nodes in a lowest hierarchy). A balanced topology of a tumor may be indicative of the absence of tumor stem cells, provided that analysis was effected for a significant number of cell divisions.

Cancer stem cell analysis effected according to the teachings of the present invention can be authenticated using marker (e.g., surface) expression. Once a tumor is characterized by the presence of stem cells, agents that target these cancer stem cells can be used and may lead to improved outcomes in the treatment of the disease.

The teachings of the present invention may be used also, in the field of oncology, for e.g., identifying the tissue origin of a cancer of unknown origin (see Example 6 of the Examples section which follows); in the field of neurobiology for e.g., identifying patterns of neuron migration; in the field of stem cell research for e.g., assessing the amount of stem cells.

The present invention also envisages performing sequential depth analyses at different stages of development (either from a single individual or from multiple individuals), to thereby obtain information regarding the growth dynamics of the analyzed cell sample, negating the need to perform analysis on single cells, and the need to perform lineage analysis.

Thus, according to an additional aspect of the present invention there is provided a method of assessing growth dynamics of a population of cells of interest (e.g., populations comprising neuronal cells or stem cells, see Example 5 of the Examples section which follows).

The method comprising determining cell depth of at least two samples of the population of cells of interest, each of said two samples being of a different age, thereby assessing growth dynamics of the population of cells of interest.

As used herein the term "age" refers to the period of time from zygote fertilization (when the population is derived from an individual) or from culture establishment (seeding).

Reagents for inferring the lineage and depth information of the present invention can be included in a kit. Such a kit may include PCR primers and optionally sequencing reagents such as provided in the Examples section which follows.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

BACKGROUND

The lineage relations between the cells that participated in the development of an organism up to a certain point in time can be represented faithfully by a rooted labelled binary tree, which is called the organism cumulative cell lineage tree (FIG. 1a). For any sample of cells of the organism, such as cells sampled from a specific organ or tissue, the lineage relations among the cells is represented by the so-called cell sample lineage tree, which is derived from the cumulative cell lineage tree (FIG. 1a), with leaves representing the sample and a root representing the least common ancestor of the sample. The cell sample lineage tree has two forms (FIG. 1b): topological—representing the lineage relation between the sample and its least common ancestor, and geometrical—representing in addition the number of cell divisions that occurred between the cells represented in the tree.

The aim of these examples was to discover whether somatic mutations in higher organisms, including Human, accumulated during normal organism development implicitly encode, and with what precision, the entire organism cell lineage tree.

FIG. 1c shows how accumulated somatic mutations may encode a cell lineage tree. If in each cell division each daughter cell acquires a new mutation, and all mutations are unique and persistent (namely there are no back-mutations[28]), then the organism cell lineage tree can be precisely reconstructed from this mutation information, using known phylogenetic algorithms[28].

However, lineage tree reconstruction may be hampered by two factors: If colliding mutations (FIG. 1d) occur during development, an incorrect tree may be reconstructed. If silent cell divisions (FIG. 1d) occur during development, the mutation information might be insufficient in order to complete the lineage tree reconstruction. Still, known phylogenetic algorithms can produce useful lineage information in spite of colliding mutations and silent cell divisions if the mutations carry sufficient information with a sufficiently high "signal-to-noise" ratio.

It should be noted however that in order to obtain a true reconstructed tree, lineage analysis of the present invention is effected at the single cell level (or groups of single cells) and not at the tissue level. While lineage relations within a group of single cells are well defined and can be unambiguously represented by a binary tree, lineage relations within a group of tissues (except for the very special case of discrete cell clones) are undefined, cannot be unambiguously represented by any mathematical entity, and may not be possible to represent at all with a binary tree.

For example, examining the lineage relationships within a group of cells from a specific organism it is always possible to represent all of these relations by a single binary tree, whose leaves are the single cells. This binary tree completely represents the lineage relations, and there is no ambiguity—there is only one tree which represents these relations, and this tree represents only such lineage relations.

The lineage relations between a group of single cells in well defined and not ambiguous. An example is illustrated in FIG. 1e, where the lineage relations within a group of three cells—blue, green and red is examined. The lineage relations are depicted by a reconstructed tree which has three leaves, one for each examined cell, and two internal nodes representing the least common ancestors (LCAs) of the cells. (LCA1 is the least common ancestor of the blue and green cells, while LCA2 is the least common ancestor of both the red and blue and the red and green cells. Note that there is only one possible tree which correctly represents the lineage relationship within the group, and this tree represents only this type of lineage relationship.

Figure 1F:
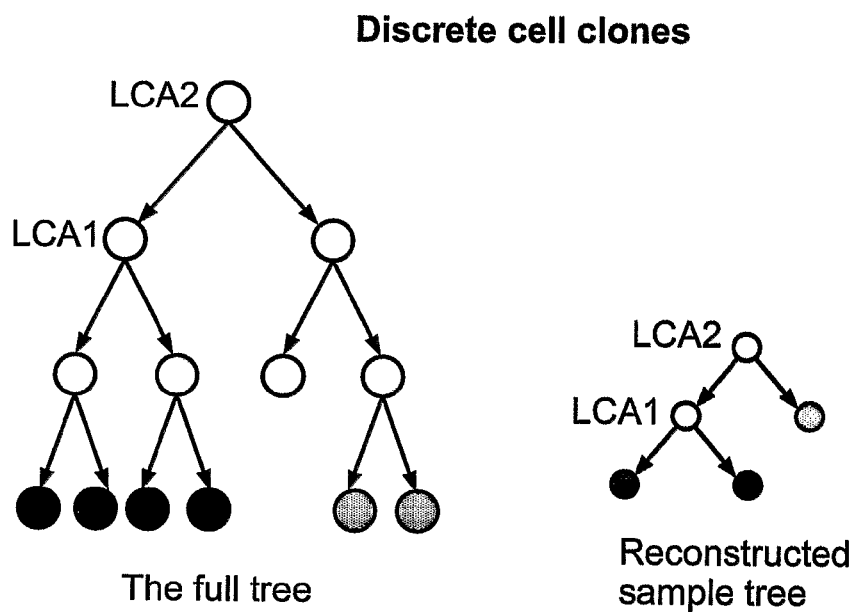

The lineage relations within a group of discrete cell clones are also well defined and unambiguous. Cell clones are groups of cells which are all descendants of a single founder cell. Clones A and B are discrete clones if the founder cell of A is not the descendant of the founder cell of B, and vice versa. Discrete cell clones are very hard to detect in vivo, but they may be produced in vitro for building of artificial trees—for control purposes. Lineage relations within a group of discrete cell clones are always well defined and unambiguous. An example is illustrated in FIG. 1f. In this example, the lineage relations within a group of three discrete cell clones, each clone comprised of two cells are examined. Because each clone is discrete, beginning in a single founder cell (depicted as a semi-transparent colored circle—notice that the founder cells are not descendants of each other), it is possible to depict the lineage relations within this group of clones by a binary tree, in an unambiguous manner. Note that this situation is analogous to single cells, because the tree of the founder cells of the clones, which are all single cells is essentially reconstructed.

Figure 1G:
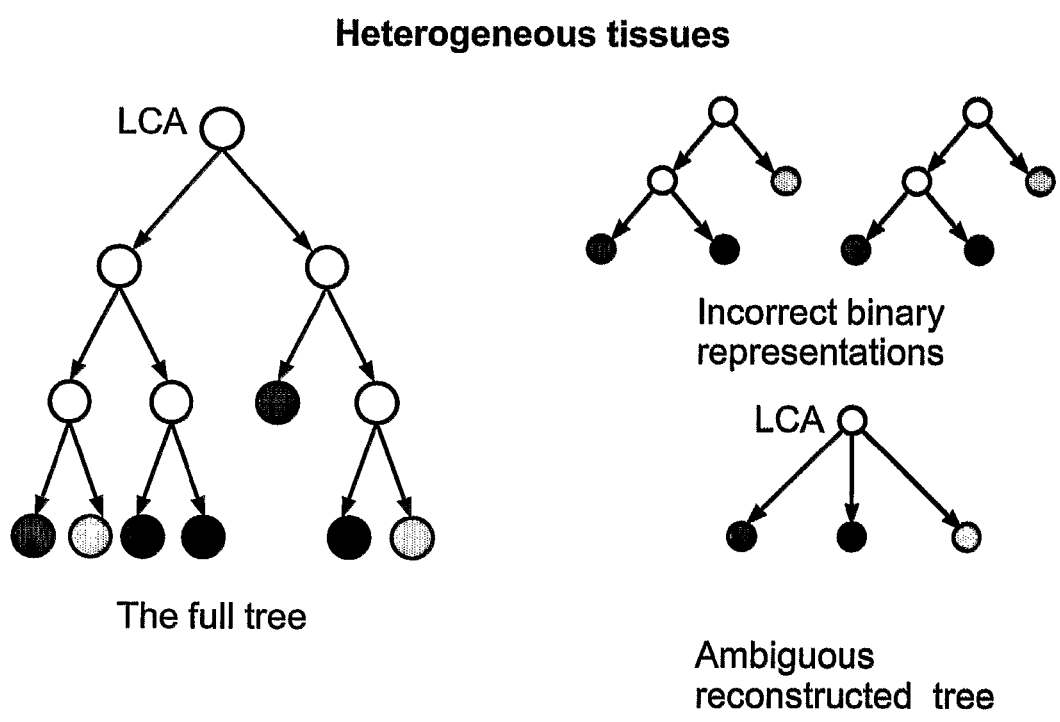

The lineage relations within a group of heterogeneous tissues are un-defined, may be ambiguous and cannot be represented by a binary tree. Heterogeneous tissues are groups of cells which are not discrete cell clones. Lineage analysis of heterogeneous tissues is represented in FIG. 1g. In this example the blue and red tissues are composed of two cells each, and the green tissue is composed of three cells. In an attempt to gain insight into the lineage relations within these tissues, it was decided that the lineage relations within the founder cells of the different tissues represent the lineage relationships within the tissues themselves. But this definition is ineffective because the founder cell of all three tissues is the same cell, the LCA. Therefore, there is no binary tree that correctly represents the lineage relations. Illustration of a non-binary tree which does represent these relations, results in a tree which is not very informative, and is also ambiguous because it represents various lineage scenarios.

Example 1

MS Mutations Serve as Sufficient Source of Variability for Reconstructing Cell Lineage Trees To determine whether MS mutations provide sufficient information for lineage tree reconstruction, the expected level of somatic MS mutations in humans and in mice was calculated. Computer simulations were used to estimate the quality of tree reconstruction based on such information.

Number of MS in Human and Mouse Genomes

The MATLAB program was written for searching MS in any sequenced genome. Genomes of several model organisms were taken from hgdownload.cse.ucsc.edu/downloads.html, and searched for all mono- to hexa-nucleotide MS that are 9 uninterrupted repeats or longer. The search was performed on one strand only to avoid counting of the complementary sequence. For any repeat unit (e.g. AAG) its frame shifts (AGA, GAA) were not searched, so results are an underestimate. Complementary sequences were searched since the search was done on one strand only (e.g. AC and GT). Repeat units that are by themselves repetitive were not searched (such as AGAG, because the MS was already discovered under AG). Table 1 below shows the number of MS in humans and mice*.

MS mutations was computed by summing the expected number of mutations in each length category. The following Table 2 summarizes these data.

TABLE 2

| | Number of repeats | | | | | | | | | |
|---|---|---|---|---|---|---|---|---|---|---|
| | <9 | 9 | 10 | 11 | 12 | 13 | 14 | 15 | >15 | All MS (>8) |
| Mutation rate | 0* | 1.0421e−006 | 5.0510e−006 | 8.8083e−006 | 1.2254e−005 | 1.7047e−005 | 2.3716e−005 | 3.2993e−005 | 3.5361e−005 | |
| Number of alleles in human genome | >1 · $10^6$ | 696034 | 457752 | 288054 | 225074 | 196330 | 173372 | 154158 | 790884 | 2981658 |
| Expected mutations in each daughter cell | 0 | 0.7253 | 2.3121 | 2.5373 | 2.7580 | 3.3469 | 4.1116 | 5.0861 | 27.9664 | 48.8437 |
| Probability for no mutations in each daughter cell | 1 | 0.4842 | 0.0991 | 0.0791 | 0.0634 | 0.0352 | 0.0164 | 0.0062 | 7.1468e−013 | 6.1554e−022 |

*In reported data (Brinkmann (1998) Supra), no MS mutations were found in this category (of MS with <9 repeats), possibly because the mutation rate is lower than the experimental detection threshold. In the present analysis, a conservative assumption was made and the rate was set to zero.

TABLE 1

| Repeat unit | Human (build 35) | Mouse (build 33) |
|---|---|---|
| Mononucleotide | 1331268 | 955804 |
| Dinucleotide | 124582 | 447394 |
| Trinucleotide | 8379 | 38807 |
| Tetranucleotide | 23398 | 93897 |
| Pentanucleotide | 2982 | 19263 |
| Hexanucleotide | 220 | 9030 |
| Total | 1,490,829 | 1,564,195 |

*—It will be appreciated that since there are two alleles of each locus these numbers should be doubled.

Estimation of the Number of MS Mutations

From analysis of published data regarding human MS mutation rates [Brinkmann, B. et al., Mutation rate in human microsatellites: influence of the structure and length of the tandem repeat Am J Hum Genet. 62, 1408-15 (1998)], the approximated rates of mutations in human MS per human generation were obtained, as a function of the length of the MS (number of uninterrupted tandem repeat units). Although the rate of mutations in MS loci is also dependent to a great extent on the specific locus examined [Ellegren, H. Microsatellites: simple sequences with complex evolution Nat Rev Genet 5, 435-45 (2004)], in this analysis the average mutation rate in each size category was determined as a first approximation to be the mutation rate obtained from (38). By dividing these rates by the approximated number of cell divisions in human male and female generations (23 for female, 350 for male) [1], the approximated rates of mutation per cell division were obtained. The MATLAB computer program was developed to search for genomes of desired sequences. This program was used to search the human genome for MS (containing basic repeat units of 1-4 base pairs), and subsequently to sort the MS according to their length. For each length, the expected number of mutations acquired by a daughter cell in a single cell division was calculated by multiplying the mutation rate by the number of MS. The total number of expected Human Wild-Type Development Model The purpose of the model is to allow calculation of the probability that during human prenatal development, in each cell division, each daughter cell acquires at least one new mutation in a MS locus. The model has two versions: an over-estimate version, which is intended to contain a larger depth and a larger number of cell divisions relative to the real (unknown) tree, and a realistic version which is intended to contain a realistic estimate of the depth and number of cell divisions relative to the real tree.

Over-Estimate Version

In this model, development starts from a single cell, the zygote, in a series of 46 binary cell divisions, producing a full depth-46 binary tree, which has $\sim 10^{14}$ leaves and $\sim 10^{14}$ internal nodes, hence it has $\sim 2*10^{14}$ nodes altogether (according to published data the adult human has $\sim 10^{14}$ cells). This series of 46 divisions lasts for 23 days because each cell cycle is exactly 12 hours long (according to published data the cell cycle in early human embryogenesis is 12-24 h). From this point on, there are additional 486 cycles of 12 h in 243 days until birth. In each cycle, each cell divides with a probability of 0.5 and dies with a probability of 0.5. Therefore the number of living cells remains relatively constant from day 23 to day 266 (birth) at $\sim 10^{14}$ and in each day $2*(10^{14})$ cells are produced. The total number of cells produced during this process, and therefore the total number of nodes in the complete cell lineage tree at birth is $\sim 2*(10^{14})+(486*(10^{14}))=4.9*(10^{16})$.

The maximum depth for a node in the tree is 532. (266*2)

The average depth for a node is 288.5 ((532+45)/2) (the average depth at day 23 is 45)

The probability for each daughter cell to not acquire any new mutations in MS loci in a single cell division is 6.1554e−022 (see 'Estimation of the number of MS mutations' section). Therefore, the probability for at least one new MS mutation in every node in the tree is $(1-6.1554e-022)^{\wedge}(4.9*(10^{\wedge}16))>0.99999$ Realistic Version In this version, the duration of each cell cycle is 24 hours. Following fertilization and creation of the zygote, 46 binary cell divisions occur in 46 days, producing a full depth-46 binary tree, which has ~10^14 leaves and ~10^14 internal nodes, hence it has ~2*10^14 nodes altogether (according to published data the adult human has ~10^14 cells). From this point on, there are additional 220 cycles of cell divisions in which, in each cycle, each cell divides with a probability of 0.5 and dies with a probability of 0.5. Therefore the number of living cells remains relatively constant from day 46 to day 266 (birth) at ~10^14 and in each day 2*10^14 cells are produced. The total number of cells produced during this process, and therefore the total number of nodes in the complete cell lineage tree at birth is ~2*10^14+(220*10^14)=2.2*10^16

The maximum depth for a node in the tree is 266.

The average depth for a node is 155.5 ((266+45)/2) (the average depth at day 46 is 45).

The probability for each daughter cell to not acquire any new mutations in MS loci in a single cell division is 6.1554e-022 (see 'Estimation of the number of MS mutations' section). Therefore, the probability for at least one new MS mutation in every node in the tree is (1−6.1554e-022)^(2.2*(10^16))>0.99999.

Thus, as shown the human and mouse ~1.5 million MS loci are interspersed on all chromosomes and range in size from 9 to 300 repeat units per MS locus. Calculations based on published data regarding human MS mutation rates (38) show that in each cell division in wild type humans, each daughter cell acquires on average ~48 new mutations in MS loci. They also show that in a single cell division the probability of a daughter cell to not acquire a new mutation is less than $10^{-21}$. In order to find out if the cumulative cell lineage tree of wild type Human newborns can be reconstructed from its genomic MS variability, a model of human embryonic development was created. The model has an over-estimation of the number of cells and cell divisions, so that it can serve as a theoretical upper-bound on the depth and size of the cumulative cell lineage tree of a newborn Human. It was found that in the model, in more than 99.9% of newborns there is at least one new mutation in each daughter cell in each cell division, suggesting that genomic variability within a newborn Human contains sufficient information to allow effective reconstruction of its cell lineage tree. However, as mentioned above, colliding mutations may cause erroneous tree reconstruction in some instances, depending mainly on the topology and depth of the tree. Because there is no data on the topology and depth of newborn cumulative cell lineage trees, it is difficult to calculate the effect that colliding mutations may have. However, it was proved analytically that in Human and Mouse lineage trees with a maximum depth of 40 cell divisions (which can contain up to 1012 leaves and correspond, under reasonable assumptions, to a newborn mouse, FIG. 2b), with any topology, colliding mutations are expected to have no effect and the tree can be reconstructed with 100% accuracy with very high probability.

Figure 2A:
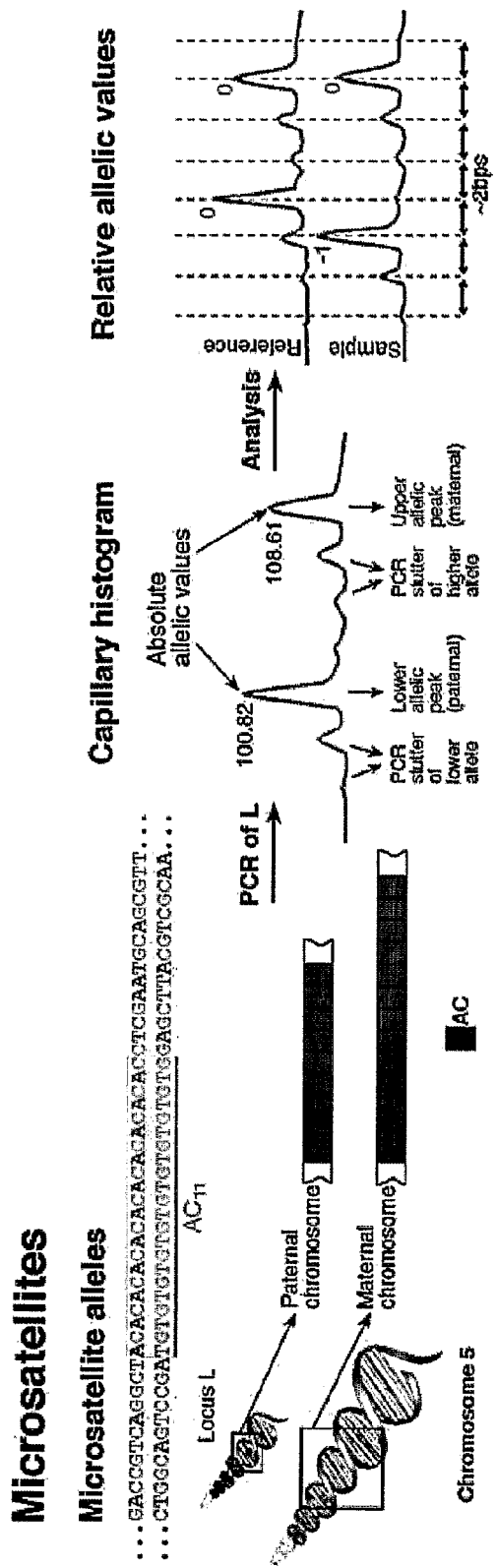
FIGS. 2a-b are annotated diagrams describing simulation of MS mutations and reconstruction score on random trees.
Figure 2B:
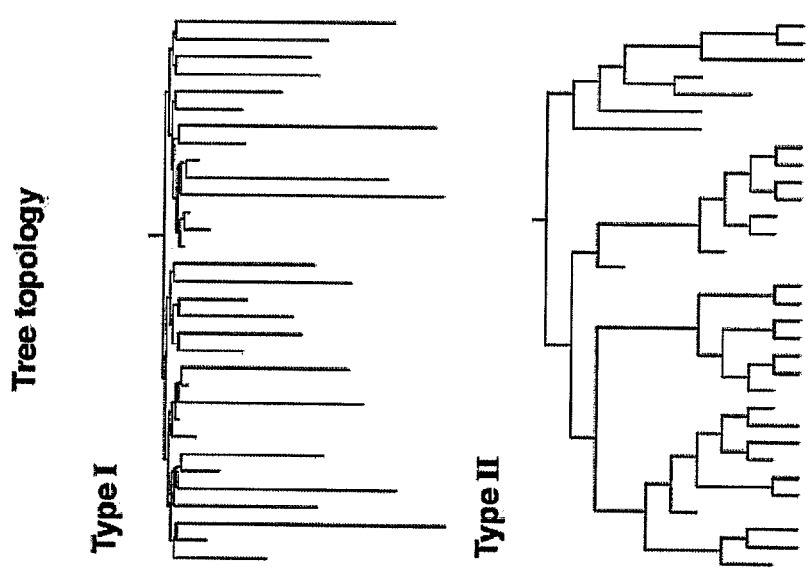
Figure 2B:
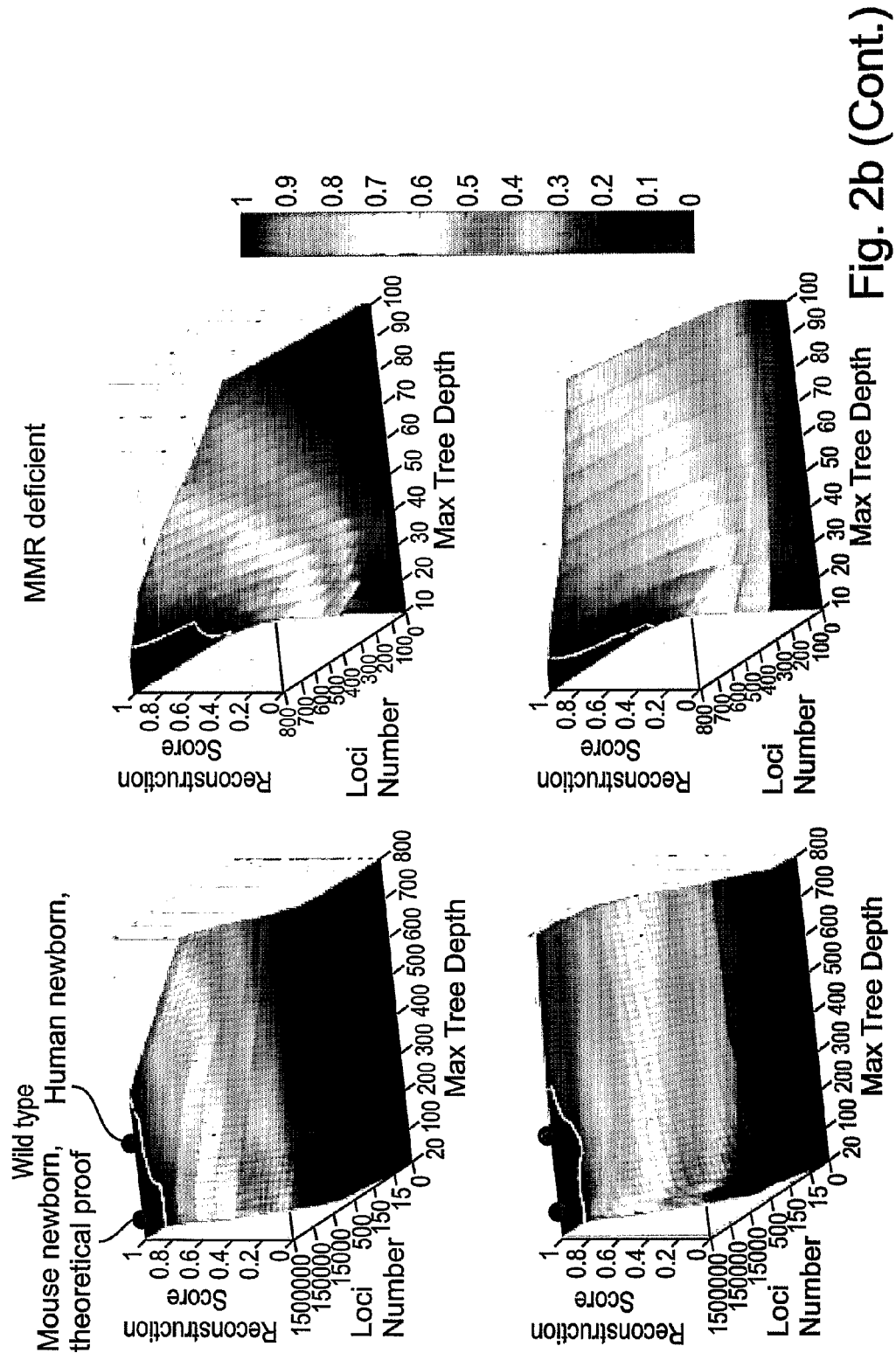

Mathematical analysis of trees deeper than 40 cell divisions is more difficult, and hence computer simulations were chosen as a preferred method of analysis. Since the topology of Human and Mouse lineage trees is not known, two types of randomly-generated trees (FIG. 2b) were focused on, and wild type and MMR-deficient mutational behaviour on hypothetical organisms that develop according to the pattern of these trees were simulated. The topological cell sample lineage tree of 32 randomly chosen cells was then reconstructed based on their identifiers. In wild type Human and Mouse, analysis of the entire set of MS yielded a complete reconstruction with 100% accuracy in trees with a depth of up to several hundred cell divisions, corresponding to adult mice and newborn humans, and highly accurate reconstructions can still be achieved even by using a small fraction of the genomic MS loci (for example, a tree of depth up to 400 cell divisions can be reconstructed with more than 90% accuracy using 10% of the genome MS loci; see FIG. 2b). In MMR-deficient organisms, analysis of only a few hundred MS is sufficient to allow accurate reconstruction of complex cell lineage trees (FIG. 2b). Simulations were performed for samples with up to 100 cells, due to the computational resources required by the phylogenetic analysis algorithm. Analysis within that range suggests that reconstruction scores may not decrease as the size of the cell sample increases.

Example 2

Cell Lineage Inference Machine

Figure 3:
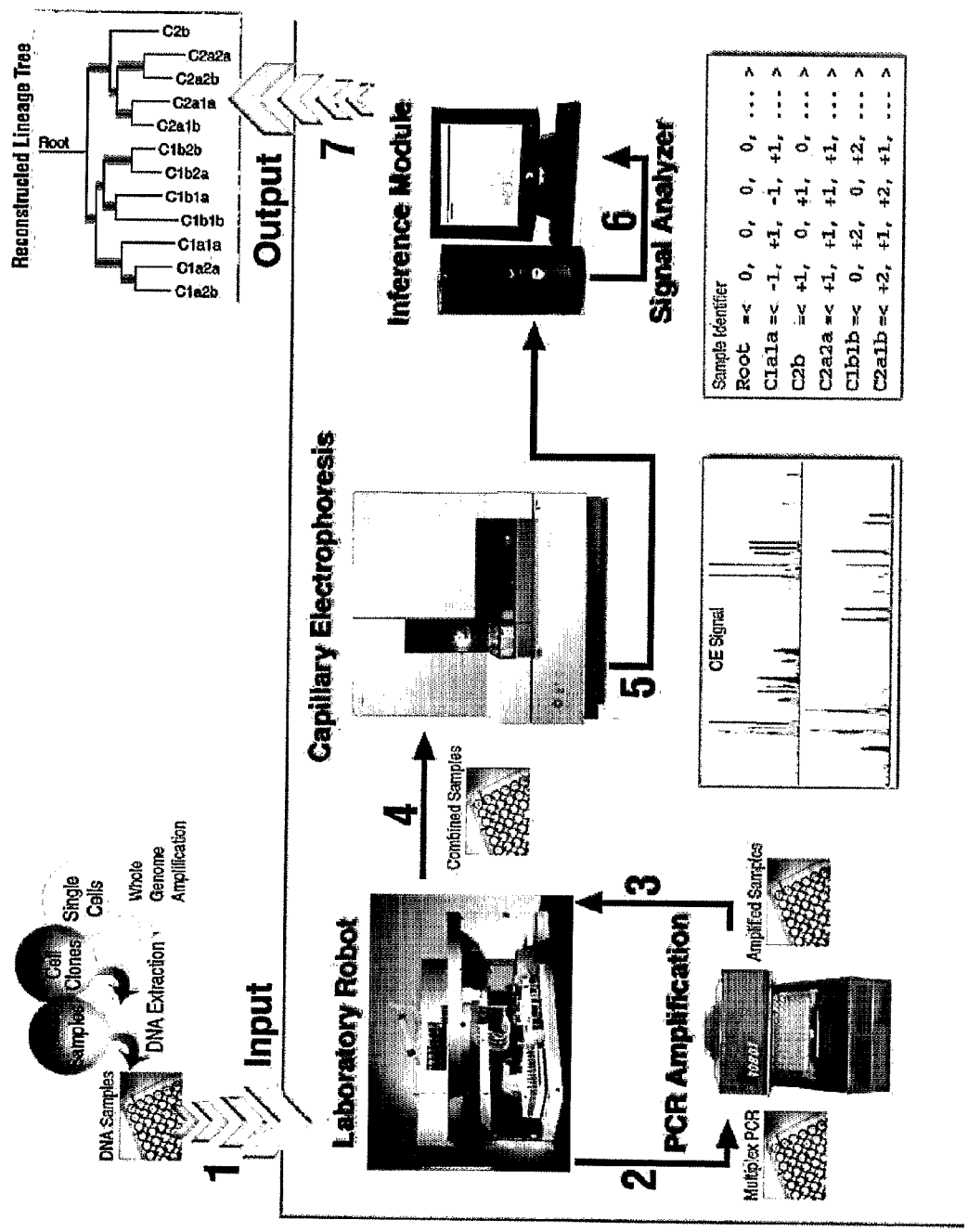
FIG. 3 is a flow chart comprising annotated diagrams and photographs describing a cell lineage inference machine. Photos of capillary machine and computer are under Copyright and provided courtesy of Applied Biosystems (an Applera Corporation Business). All rights reserved.

A procedure was developed that takes as input a set of DNA samples, primers for MS loci, information on expected MS sizes, and information on PCR and capillary electrophoresis multiplexing compatibility between MS loci, and outputs a reconstructed geometrical cell lineage tree correlated with the DNA samples. The procedure is oblivious to the DNA source, which may be from clones of a single cell, from tissue samples, or from single cells. The procedure involves common lab protocols, including PCR and capillary electrophoresis, and known algorithms, including a phylogenetic analysis algorithm. The procedure is realized in a hybrid in vitro/in silico Cell Lineage Inference Machine (FIG. 3). The machine operates as follows. First, a predetermined set of n MS loci is amplified from each sample by multiplex PCR and run on a capillary machine, yielding several histograms for each sample as seen in FIG. 2a.

A programmable laboratory robot augmented with a PCR machine performs the liquid handling for PCR, the PCR itself, and the preparation of the samples for the capillary machine. Sample analysis by the capillary machine produces histograms, which are analyzed by a computer program that utilizes a signal processing algorithm to assign relative allelic values to all the MS loci in all samples. Subsequently, each sample is assigned an identifier—a vector of its 2n relative allelic values. Finally, a computer program applies a phylogenetic algorithm to the set of sample identifiers and produces a reconstructed tree associated with the DNA samples. In this work, DNA samples were extracted from cell clones (with automatic signal analysis) and from heterogeneous tissue samples (with manual signal analysis). As yet, the procedure has not been tested with DNA samples extracted and amplified from single cells[39]. Details of the components of the cell lineage inference machine are presented below.

1. Robotic PCR Preparation

The input includes a plate with extracted DNA samples (FIG. 3, Channel 1), a plate with MS loci primers set, a tube of PCR reaction mix (dNTPs, hot-start enzyme, buffer), a trough of DDW, a file describing the multiplex PCR primer groups (including both a list of primer pairs and groups and concentrations of multiplex PCR) and a file of the DNA sample name. The output comprises a PCR plate with amplification reaction of a set of samples on a set of MS loci (FIG. 3, Channel 2).

The plates and tubes were loaded to the robot work table. A program compiled the input files and generated a robot program which is executed by the Tecan genesis robot.

Primers for most MS loci were designed using Primer3 (frodo.wi.mit.edu/cgi-bin/primer3/primer3_www.cgi) with the following parameters changed from default: Primer size=20, 22, 27 (minimum, optimal, maximum); Primer Tm=62° C., 65° C., 68° C.; Max Tm difference=2.5° C.; CG clamp=1. Some primers were taken from STRbase (www.c-stl.nist.gov/biotech/strbase/).

2. PCR Amplification

The input includes both a PCR plate with amplification reaction of a set of samples on a set of MS loci (FIG. 3, Channel 2) and a PCR program. The output is a PCR plate with amplified MS loci for each sample (FIG. 3, Channel 3).

The PCR plate is loaded by the robot to robotic thermo-cycler (Biometra TRobot). The PCR program is then called and executed automatically.

In each amplification reaction, 3-6 MS loci were amplified together in a multiplex reaction. TCT reactions (as described in the next example) were performed in 50 µl including 100-125 ng DNA, 0.1-0.5 µM of each primer, 0.2 mM of each dNTP, and 1.25 U of AmpliTaq Gold polymerase (Applied Biosystems).

Thermal cycling conditions for TCT were: (i) 95° C. for 10 min, (ii) 35 cycles: 95° C. for 1 min, 58° C. for 1 min, 72° C. for 1 min, (iii) 72° C. for 45 min, (iv) 16° C. hold. *Arabidopsis* reactions were performed in 20 µl including 4 µl DNA, 4 µl primer mix (0.157-1.56 µM concentration of each primer) and 8 µl reaction mix from the Extract-N-Amp kit. Thermal cycling conditions for *Arabidopsis* were: (i) 95° C. for 10 min, (ii) 35 cycles: 95° C. for 1 min, 58° C. for 1 min, 65° C. for 2 min, (iii) 65° C. for 45 min, (iv) 4° C. hold. Thermal cycling conditions for *Robinia* are as described in [45].

3. Robotic Capillary Electrophoresis Sample Preparation

The input includes a PCR plate with amplified MS loci for each sample (FIG. 3, Channel 3), a file describing the multiplex PCR primer groups (including the dilution rate of groups and the grouping for CE runs), a file of the DNA sample name, a tube with formamide+Liz standard size marker (Applied Biosystems), a trough of DDW and an ABI 3100-Avant plate. The output includes a CE plate with samples ready for Capillary Electrophoresis (FIG. 3, Channel 4) and a CE plate file describing the amplified samples and loci groups in each well. (FIG. 3, Channel 4).

The amplified sample plate is off loaded by the robot from the thermo-cycler and placed on the worktable. Each reaction is diluted and combined with other amplification reaction of the same sample on other loci. Dilution rates and combined groups are taken from the loci data file. 3 micro litter of the combined diluted sample is than diluted with 15 micro litter of formamide Liz marker in the CE plate. A program then generates a CE plate file.

4. Capillary Electrophoresis Machine

The input includes a CE plate with samples ready for Capillary Electrophoresis. (FIG. 3, Channel 4) and a CE plate file describing the amplified samples and loci groups in each well. (FIG. 3, Channel 4). The output includes a file with CE signal sizing table as exported from GeneMapper (FIG. 3, Channel 5)

Amplified products are run on a capillary electrophoresis machine (ABI Prism 3100-Avant Genetic Analyzer, Applied Biosystems) and fragment analysis is performed using the GeneMapper v3.5 software accompanying the machine. This package enables high resolution analysis and can separate between amplified products with a 1 bp difference for fragments lengths up to several hundred of bps. The GeneMapper sizing table is exported to a file.

5. Capillary Electrophoresis Signal Analyzer

The input includes a file with CE signal sizing table as exported from GeneMapper (FIG. 3, Channel 5) and a loci database (including the loci name, loci MS repeat length, the reference length for both alleles (obtained manually from arbitrary sample usually the root) and the Loci CE colour). The output includes a sample identifier data file (FIG. 3, Channel 6). In this file, each sample has identifier which is a vector of the relative allelic values for all loci on both alleles. Also, each null value is assigned if amplification failed for a specific allele. Also included are reports of signal analysis problems for manual control.

The signal analyzer is software that converts the CE signal to a mathematical identifier for each sample. Due to a large amount of capillary electrophoresis data and since MS amplification often results a complex stutter pattern of several peaks, there is a need for automatic CE signal processing algorithm. An automatic algorithm has been developed that detects what is the relative allelic value of each allele of each sample and resolves the stutter pattern and signal overlaps between two close alleles. The algorithm was calibrated according to a manual analysis of tree TCT-A (see Example 3 below) and has reached 97% accuracy when compared to the manual analysis. Tree TCT-B (se Example 3 below) was analyzed completely by the automatic software. Tree TCT-C was analyzed by the automatic algorithm software and results were compared to a complete manual analysis with accuracy of 91%. The algorithm generates relative allelic values for each sample and loci assuming the upper signal is referring to the upper allele and the lower signal referring to the lower allele and ignoring the crossover problem which was assumed to be rare and with low impact.

Algorithm Description: the correct capillary electrophoresis histogram (CEH) of both alleles of the locus according to CE-run file the locus color and typical reference length for each allele is retrieved. All relevant peaks within a given window of WINDOW_SIZE repeats around the typical length of the allele are then retrieved. If no signal exists a null value is assigned and a warning is given.

The CEH is then assigned to bins of the size of the repeat length. Each bin maximal peak value is selected as the bin value. Each bin is associated with allelic value (i.e. −2+10 etc) relative to the reference.

The method detects if there is an overlap between the CEH of upper allele and lower allele. If no overlap exists the highest peak of each allele is selected and its bin relative allelic value is assigned to the identifier.

The peaks that are less than PEAK_THRESHOLD of the maximal peak within the window are considered noise and are filtered. Then the method identifies candidate peaks that are local maxima within the signal window. If more than two candidates exist the two candidates that are closer to the reference are selected.

If any of the alleles have two candidates the upper candidate allelic value is assigned to the upper allele and the lower candidate allelic value is assigned to the lower allele. In this case if the other allele has only one candidate peak its relative allelic value is assigned for this allele.

If one candidate exist for both alleles the following are possible:

1. The peaks are different from each other. In this case the peak is selected and its relative allelic value is assigned.

2. The peaks are the same, a case which requires stutter pattern resolution as follows: the two following conditions are evaluated:

Condition 1: The peak adjacent to the max from the right is bigger than UPPER_THRESHOLD of the max peak.

Condition 2: The peak adjacent to the max from the left is bigger than LOWER_THRESHOLD of the max peak.

If both conditions are false a homozygote is assumed and relative allelic values are assigned accordingly.

If condition 1 is true the max peak is selected for the lower allele and the peak adjacent from the right is selected for the upper allele. If also condition 2 is true than a warning is issued and the case is considered ambiguous.

If condition 1 is false and condition 2 is true the max peak is selected for the upper allele and the peak adjacent from the left is selected for the lower allele.

There are cases where only one allele is amplified and creates the impression of homozygote. It is highly unlikely that mutation of homozygote will change simultaneously in both alleles to the same direction in all samples. In such a case the signal is considered as single allele and zero is assigned as the other relative allelic value for all samples. This is done to avoid overestimation of mutations that occur in one allele and consider them twice for inference purposes.

Parameter defaults include PEAK_THRESHOLD 0.25, UPPER_THRESHOLD 0.3, LOWER_THRESHOLD 0.75 and WINDOW_SIZE 4.

6. Inference Module

The input is a sample identifier data file. (FIG. 3, Channel 6) and the output is a lineage relation tree of the input DNA samples including bootstrap values of internal tree edges.

For each tree (TCT or simulated tree) a distance matrix was generated by applying a distance function to all pairs of identifiers from the set of root and all leaves. The 'equal or not' distance function was used, which is the sum of differing values between two identifiers (even though it was known that a distance function taking into account the step-wise nature of MS mutations may yield better results, but it was decided at this stage to use a function that assumes as little as possible). This matrix was used as input to a program implementation the phylogenetic algorithm Neighbor-Joining (NJ). This is a MATLAB implementation as well as a web-based implementation: bioweb.pasteur.fr/seqanal/phylogeny/phylip-uk.html. The un-rooted output tree was rooted from the node corresponding to the root, yielding the reconstructed tree (which also includes edge lengths). Tree reconstructions without using the root were performed in a similar fashion, yet instead of rooting the tree from the root, the tree was rooted at the midpoint of the longest path from among all possible pathways between any two leaf nodes.

In each reconstruction (TCT or simulated tree) the reconstructed tree and real tree were compared using Penny and Hendy's topological distance algorithm (implemented using MATLAB). In this algorithm each internal edge confers a partitioning of the tree root and leaves into two groups by removing the edge. A score was assigned equal to the number of equal partitions of the two trees (modified from the original algorithm in which the score is twice the number of different partitions, and which deals with un-rooted trees).

In the TCTs, bootstrapping was assigned a measure of reliability to internal edges. Initially, the tree was reconstructed as described above. Then, the set of identifiers was used to create n pseudosamples. In each pseudosample, m loci (m=number of loci in the identifiers) were randomly chosen (with replacement), and a bootstrap tree was built using the same reconstruction method used for the initial reconstruction. Consequently, each internal edge in the reconstructed tree was assigned a number equal to the percentage of bootstrap trees in which the edge exists.

Reconstructed trees were converted to the Newick tree format using a MATLAB program. Phenograms were created from these strings using the 'drawgram' option in the website shown previously.

Example 3

Human Tissue Culture Experiments

Figure 4A:
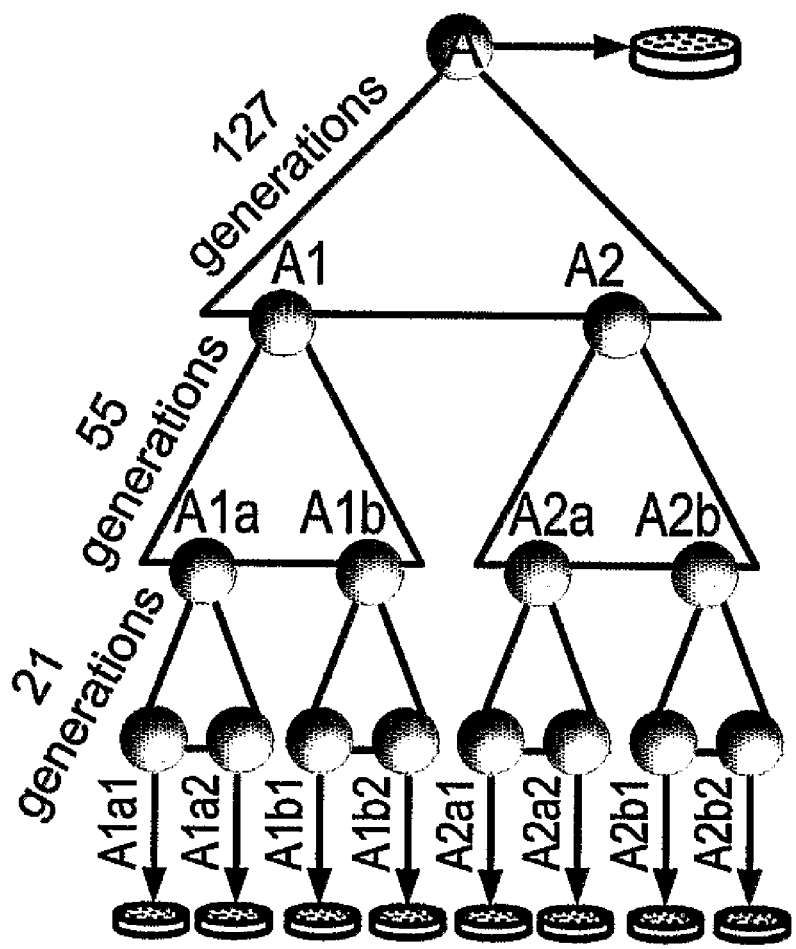
FIGS. 4a-f are combinations of annotated diagrams and graphs displaying various features of a tissue culture tree (TCT) model system.

To quantitatively evaluate the cell lineage tree reconstruction procedure, cell lineage trees were generated in vitro with known topologies and well-estimated edge lengths, called Tissue Culture Trees (TCTs), using methods as detailed below. Initially, a single cell isolated from a cell stock, defined as the tree root (node A, FIG. 4a), is allowed to proliferate for a desired number of cell divisions. Then, two cells are isolated from the root progeny, and are defined as its daughter cells in the tree (A1 and A2). This procedure is repeated by considering each daughter cell as a root of a new sub-tree, until the entire tree is grown. The tree root and leaf cells are cloned in plates and lineage analysis is performed on the DNA samples obtained from these cell clones. Using DNA sampled from cell clones instead of directly from the cells is not expected to affect analysis results. For control purposes DNA can also be obtained from the internal nodes of the sample tree, but information was not used from such DNA in the reconstruction procedure.

Figure 4B:
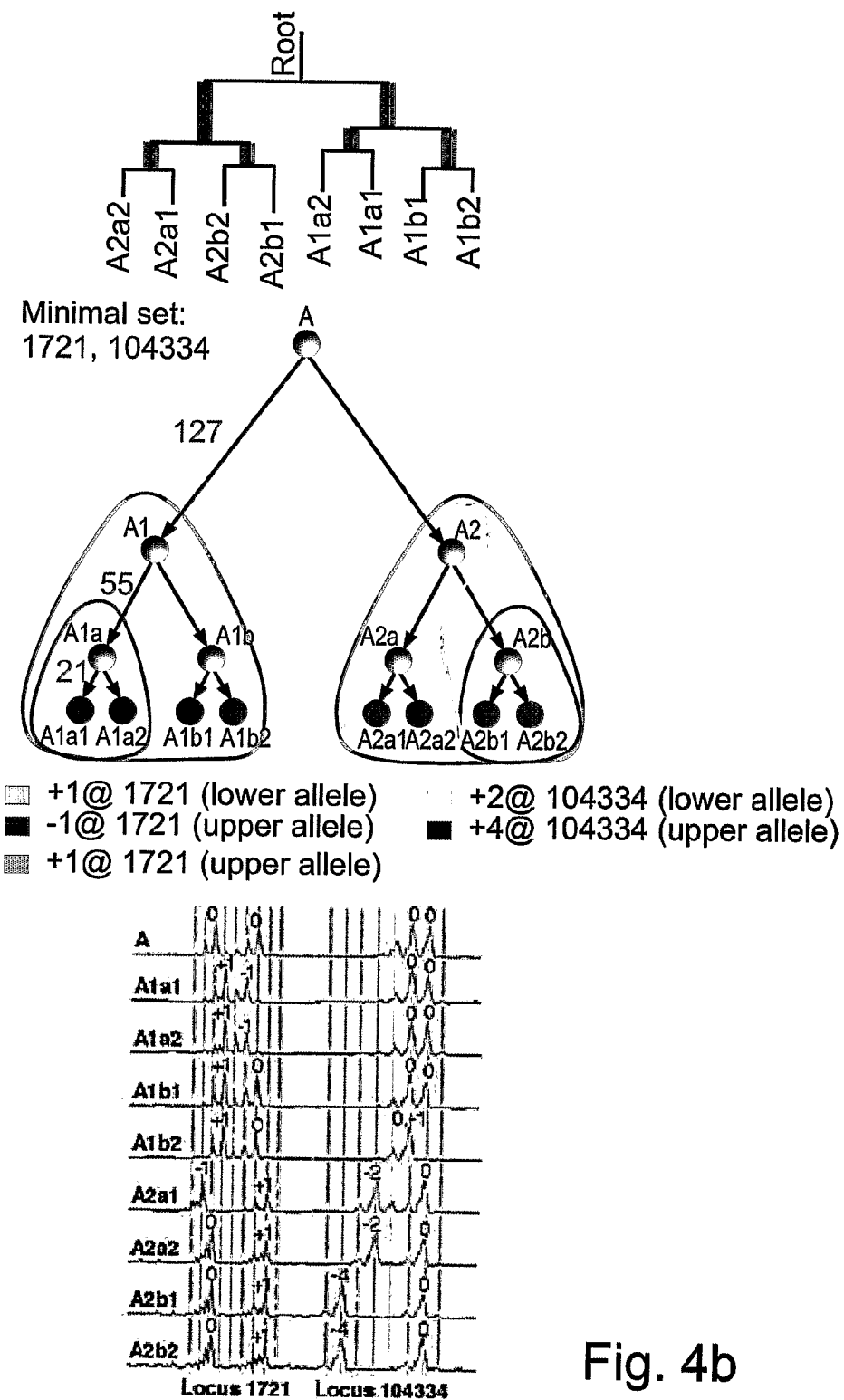
Figure 4C:
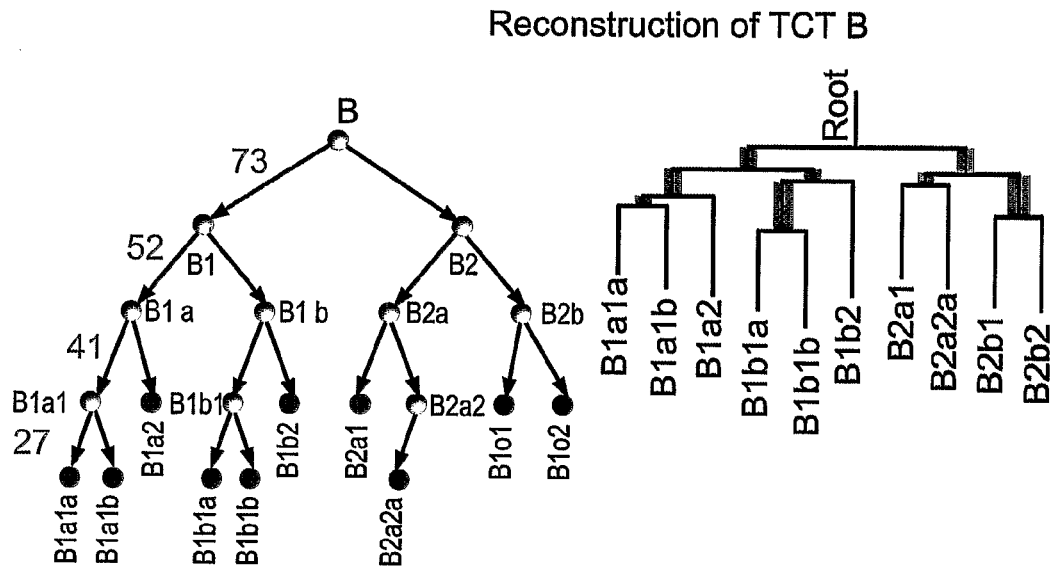
Figure 4D:
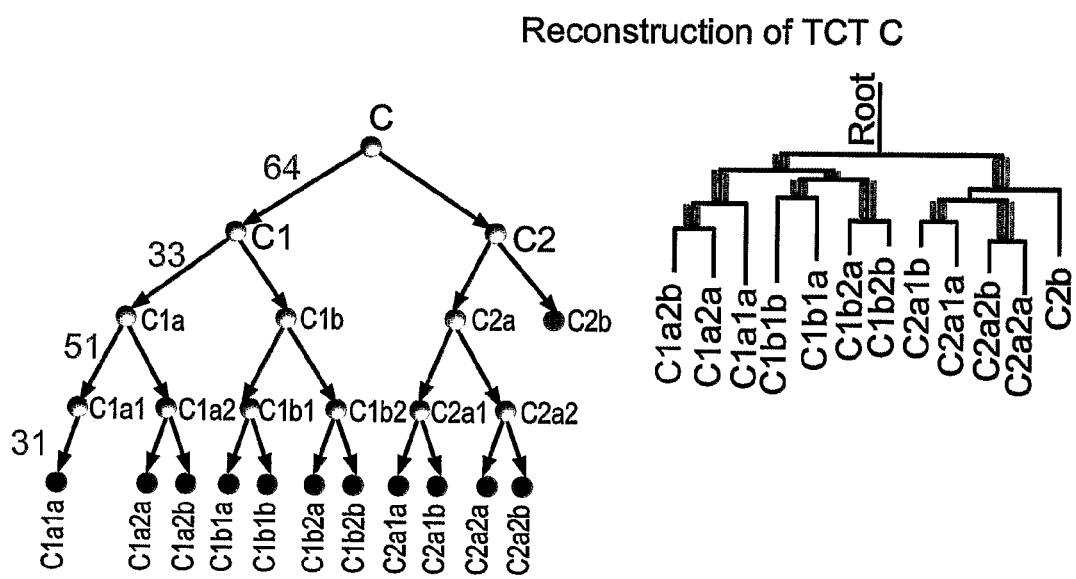

Three TCTs were constructed (A-C; FIG. 4b-d, using human adenocarcinoma cells (LS174T, ECACC), which have a mutation in a key MMR gene[40] and high MS mutation rates[41]. A set of 51 MS loci of various repeat types was chosen as detailed in table 3 below.

TABLE 3

| Locus # | Locus name | Repeat unit | SEQ ID NO: | Primers (5'->3') |
|---|---|---|---|---|
| 1 | 1721 | CT | 1 | 1721F = Gggccttcttatattgcttc |
|   |      |    | 2 | 1721R = GGAAAGACTGGACCAAAGAG |
| 2 | 352 | GT | 3 | 0352F = CTGGGAAGTTCAAGTGGCTGTG |
|   |     |    | 4 | 0352R = ATCACTGCCTGGAAGCGACAC |
| 3 | D4S3042 | AC | 5 | D4S3042F = AGCTAACTACTCTCCACCCATAC |
|   |         |    | 6 | D4S3042R = CCATGCTAAGTTTATGATGTCTG |
| 4 | 2868 | AC | 7 | 2868F = TTCCCCAATCTCACCGTCACTC |
|   |      |    | 8 | 2868R = GGCCTAGCACCTCACCTTTTCC |
| 5 | 8709 | GT | 9 | 8709F = ATCATGCAGACCCTGCCTCAAG |
|   |      |    | 10 | 8709R = ACTGTGGCATCTCCCCTAGCAG |
| 6 | CSF | AGAT | 11 | CSF-F = GGAGCAGAGGAGGTGGCAGAAG |
|   |     |      | 12 | CSF-R = ACACTTGGACAGCATTTCCTGTGTC |
| 7 | 3866 | AAG | 13 | 3866F = TTGCCAGAACATTAAGTTAGAATTTGC |
|   |      |     | 14 | 3866R = TTTGCCCTCTAGCATTTTTCACC |

TABLE 3-continued

| Locus # | Locus name | Repeat unit | SEQ ID NO: | Primers (5'->3') |
|---|---|---|---|---|
| 8 | D16S539 | AGAT | 15 | D16S539F = ACAAAAAGCCCCAGGGGTTAAGT |
| | | | 16 | D16S539R = ACCATTTAGCGTTTGTGTGTGCAT |
| 9 | 7514 | AAG | 17 | 7515F = TGCGGGTCAGAAAACAAGTCTC |
| | | | 18 | 7514R = CTGTCTAGCCCATTCCTGTTGAC |
| 10 | 9607 | CTT | 19 | 9607F = TTTTCACTTGATCCTGCACCAATC |
| | | | 20 | 9607R = TTCCACTTTTGCCCAGAGATAAC |
| 11 | D5S2084 | TC/AC | 21 | D5S2084F = AGCTGCTTACCACGAATGTC |
| | | | 22 | D5S2084R = TCAGACTTTGAGCCCTGCTA |
| 12 | D12S86 | AC | 23 | D12S86F = AGCTAGTCTGGCATGAGCAG |
| | | | 24 | D12S86R = CTATCCCCTGATGATCTCCC |
| 13 | 7959 | GT | 25 | 7959F = GTCAGTGCTCAGGCTGAACTGC |
| | | | 26 | 7959R = TCTGCCTCCTCCATTCCGTTAC |
| 14 | 8653 | A | 27 | 8653F = CGGTTACAAGCTCCACAGCAATC |
| | | | 28 | 8653R = TGACACAGAGAGGGAATCCTCGTAG |
| 15 | 9847 | AC | 29 | 9847F = TGGGTCACATCCTACCAACCAC |
| | | | 30 | 9847R = AGGCCAACAAGCAAAATCAAGG |
| 16 | 3326 | AAG | 31 | 3326F = CCTTTTCATGTTTGCTCGCTTG |
| | | | 32 | 3326R = CCCACTCAATCCTGATGAATGACC |
| 17 | 707 | AAG | 33 | 0707F = CACCGCTGGCAGTTCTTTTC |
| | | | 34 | 0707R = AGCAAACACAAGGTTAAGAATCACG |
| 18 | 6458 | AAG | 35 | 6458F = TGAGATGGGAGAAGGGAGAATCAC |
| | | | 36 | 6458R = GGCGCTTTCCAGTTACTGTTTG |
| 19 | 104439 | TTC/CCT | 37 | 104439F = CCTGGTTCTTGCTATGGCAAATG |
| | | | 38 | 104439R = CTAATCTGCTCCTCACACTACAC |
| 20 | 6005 | AC | 39 | 6005F = GCTGGTGCAGGAACAGTTGG |
| | | | 40 | 6005R = GGCTGCTCTGGCTTTAAGTTCC |
| 21 | AC49 | AC | 41 | AC49F = CGCACACGGGCAAGAGTAAGAC |
| | | | 42 | AC49R = AGGATTCGGGTGGGGCAAGG |
| 22 | dxs556 | AC | 43 | DXS556F = GCATCCCTAGATACAGTTTGGC |
| | | | 44 | DXS556R = GCCAACTTAGAAAACAGCAGGGC |
| 23 | AAG30 | AAG | 45 | AAG30F = CACAGCCTGGGAGACAAGAGTG |
| | | | 46 | AAG30R = TGCCATCAGTAGAAGCATGAGG |
| 24 | 5284 | CTG | 47 | 5284F = GAGGCTGCAGCTGCTATTCAAAG |
| | | | 48 | 5284R = CAATGCCATTCCTGCCATCTC |
| 25 | 5106 | AC | 49 | 5106F = GGAGGTGCTCAGCCATATTTGC |
| | | | 50 | 5106R = TGACAGCTCTACACCGAATTATTTGC |
| 26 | 8392 | CTT | 51 | 8392F = GAAAGACCAGATATGGTTTGCCTTC |
| | | | 52 | 8392R = AGCAATCCGGGAACACTTCATC |
| 27 | 8333 | AGAA | 53 | 8333F = GAGCCATGTTCATGCCACTG |
| | | | 54 | 8333R = CAAACCCGACTACCAGCAAC |
| 28 | 7381 | AAAGG | 55 | 7381F = CTGGGAGTCAGAAGTTGCAATG |
| | | | 56 | 7381R = GCCTCATCTCCTGTCCTGCAC |
| 29 | 5994 | AC | 57 | 5994F = GCCAAGGCAGGAAGATCACTTG |
| | | | 58 | 5994R = CCCTTTCTTCCACACACCCATC |
| 30 | 5802 | AC | 59 | 5802F = CCCAGACCAAGAACCAACTTGC |
| | | | 60 | 5802R = ATATGGTCCGGGATGCAAATG |
| 31 | TP53 | AC | 61 | TP53F = AGGGATATTCAGCCCGAGGTG |
| | | | 62 | TP53R = ACTGCCACTCCTTGCCCCATTC |
| 32 | 6424 | AC | 63 | 6424F = AAATTGGGCCAGTGGTTTATCC |
| | | | 64 | 6424R = CCACTGGGGTGTGTGTGTAG |
| 33 | 2068 | GT | 65 | 2068F = GGGCAGTCGCTACAAAGGTTTC |
| | | | 66 | 2068R = TGATGGCTTCTGATTACATATTCCTTG |

TABLE 3-continued

| Locus # | Locus name | Repeat unit | SEQ ID NO: | Primers (5'->3') |
|---|---|---|---|---|
| 34 | 9804 | AGAGG | 67 | 9804F = GCAACAAGAGTGAAGCTCCTTCTCAG |
|  |  |  | 68 | 9804R = GTCCGTGATCTGCCCGCTTC |
| 35 | 7509 | AAG | 69 | 7509F = AATTGCCATTGCAACCACATTG |
|  |  |  | 70 | 7509R = TGGCACCAGTGAGGGTCTTATTG |
| 36 | AAG44 | AAG | 71 | AAG44F = AATCCTTTGAACCCAGGAGG |
|  |  |  | 72 | AAG44R = GAGGGTTTGGTGTGTGTTAGTATTC |
| 37 | 6248 | CTT | 73 | 6248F = AGCAGCTTGGATCACTGGTGTG |
|  |  |  | 74 | 6248R = AATCTGGAGGCGAAAATTGCAG |
| 38 | HEXMUL | AGAGGG | 75 | HEXMUL-F = CCGTCTCCACCAAAACCAGTC |
|  |  |  | 76 | HEXMUL-R = ACCCAACACCCTGCTGCTTC |
| 39 | 104334 | AAG | 77 | 104334F = CTTGAACCCGGGAGGTGGAG |
|  |  |  | 78 | 104334R = GGCTCATTAAGGACCTTTTGGG |
| 40 | D21S11 | TCTA/TCTG | 79 | D21S11F = ATATGTGAGTCAATTCCCCAAG |
|  |  |  | 80 | D21S11R = TGTATTAGTCAATGTTGTCCAG |
| 41 | BAT40 | A | 81 | BAT40F = ATTAACTTCCTACACCACAAC |
|  |  |  | 82 | BAT40R = GTAGAGCAAGACCACCTTG |
| 42 | FGA | TTTC/TTCC | 83 | FGA-F = GCCCCATAGGTTTTGAACTCA |
|  |  |  | 84 | FGA-R = TGATTTGTCTGTAATTGCCAGC |
| 43 | D8S1179 | TCTA/TCTG | 85 | D8S1179F = TTTTTGTATTTCATGTGTACATTCG |
|  |  |  | 86 | D8S1179R = CGTAGCTATAATTAGTTCATTTTCA |
| 44 | D13S317 | TATC | 87 | D13S317F = ACAGAAGTCTGGGATGTGGA |
|  |  |  | 88 | D13S317R = GCCCAAAAAGACAGACAGAA |
| 45 | VWA | TCTA/TCTG | 89 | VWA-F = CCCTAGTGGATGATAAGAATAATCAGTATG |
|  |  |  | 90 | VWA-R = GGACAGATGATAAATACATAGGATGGATGG |
| 46 | D7S820 | GATA | 91 | D7S820F = TGTCATAGTTTAGAACGAACTAACG |
|  |  |  | 92 | D7S820R = CTGAGGTATCAAAAACTCAGAGG |
| 47 | D5S818 | AGAT | 93 | D5S818F = GGGTGATTTTCCTCTTTGGT |
|  |  |  | 94 | D5S818R = TGATTCCAATCATAGCCACA |
| 48 | TPOX | AATG | 95 | TPOX-F = CACTAGCACCCAGAACCGTC |
|  |  |  | 96 | TPOX-R = CCTTGTCAGCGTTTATTTGCC |
| 49 | TH01 | AATG | 97 | TH01F = GTGGGCTGAAAAGCTCCCGATTAT |
|  |  |  | 98 | TH01R = ATTCAAAGGGTATCTGGGCTCTGG |
| 50 | D3S1358 | TCTA/TCTG | 99 | D3S1358F = ACTGCAGTCCAATCTGGGT |
|  |  |  | 100 | D3S1358R = ATGAAATCAACAGAGGCTTG |
| 51 | 7401 | AAG | 101 | 7401F = TCACACAGCTGTTAAGTGGCAGAG |
|  |  |  | 102 | 7401R = CATGCCCTGTTCCCTGCTAAAG |

Figure 6:
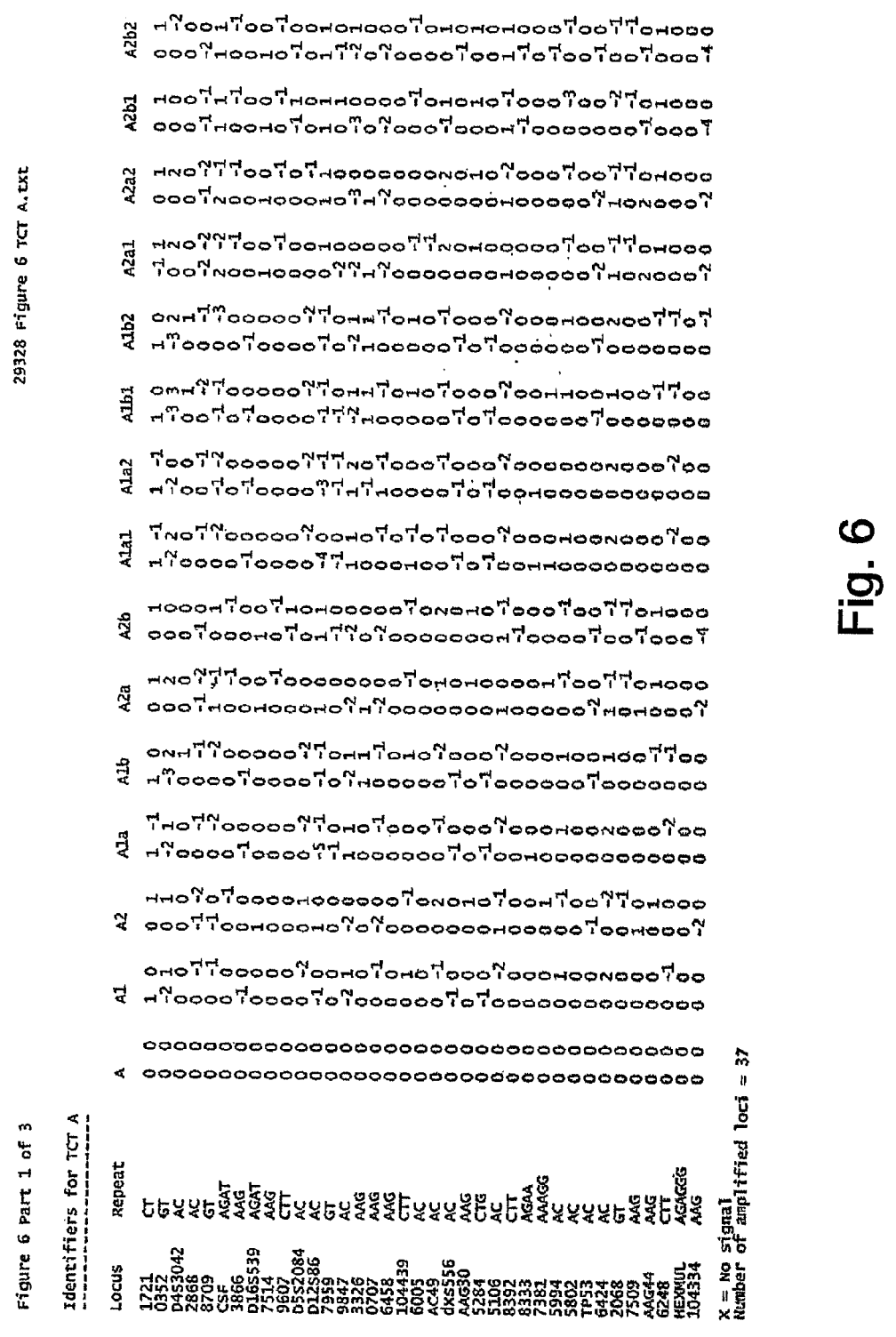
Figure 6:
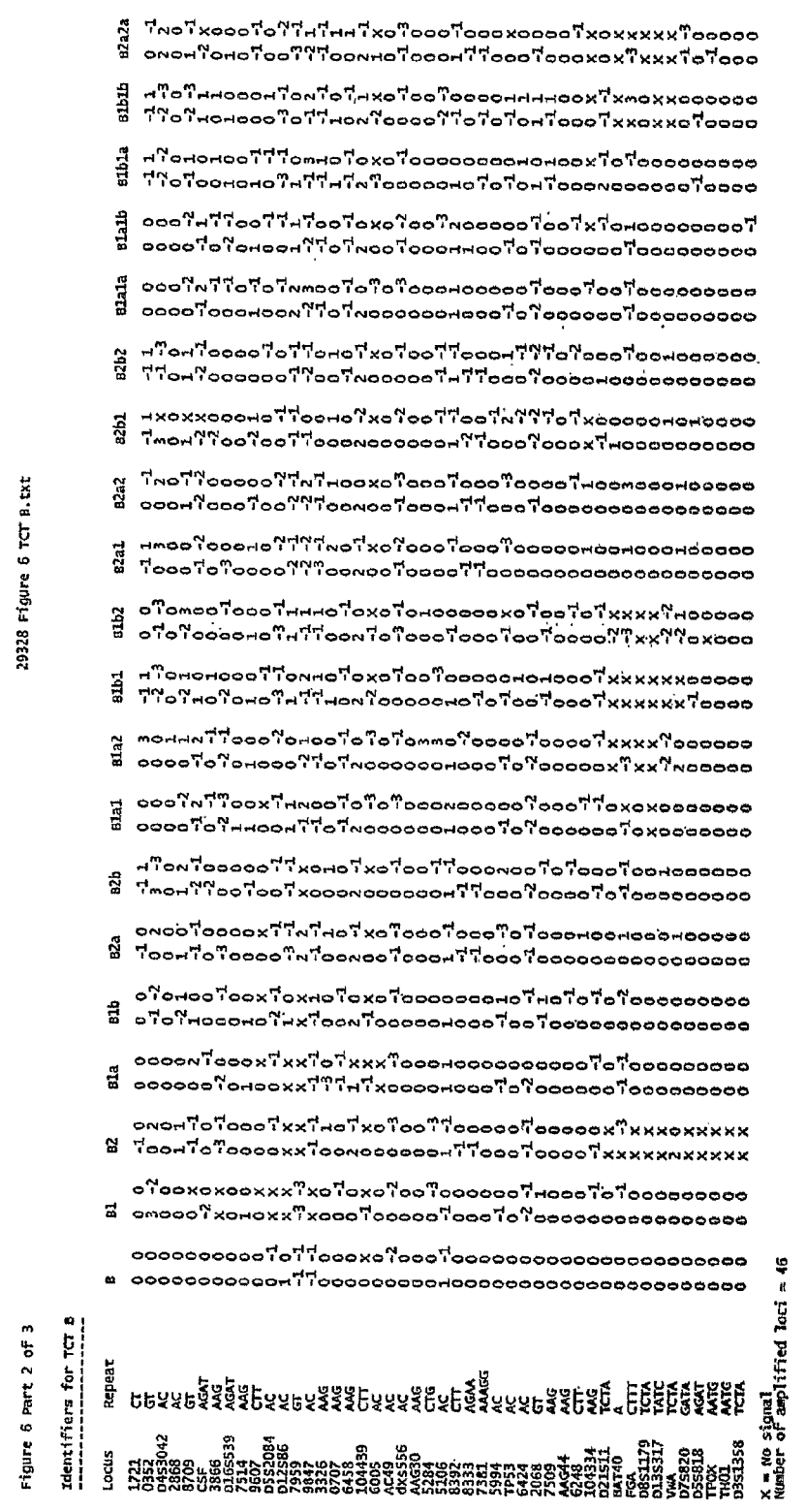
Figure 6:
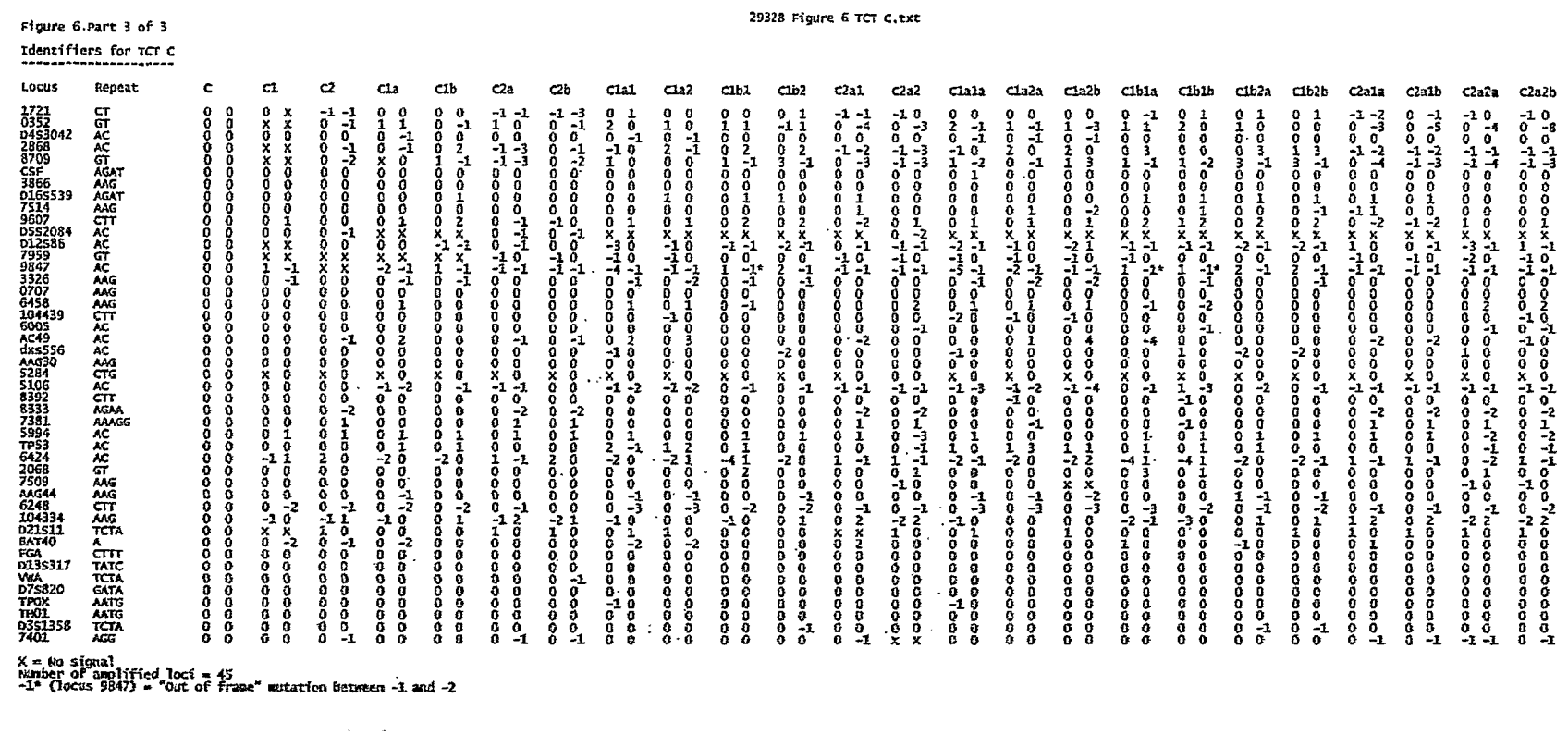

DNA samples obtained from the root and leaf nodes were fed into the Cell Lineage Inference Machine yielding a reconstructed tree for each TCT. The raw data of all the cell identifiers for TCT A, TCT B, and TCT C obtained is presented in FIG. 6.

Figure 4E:
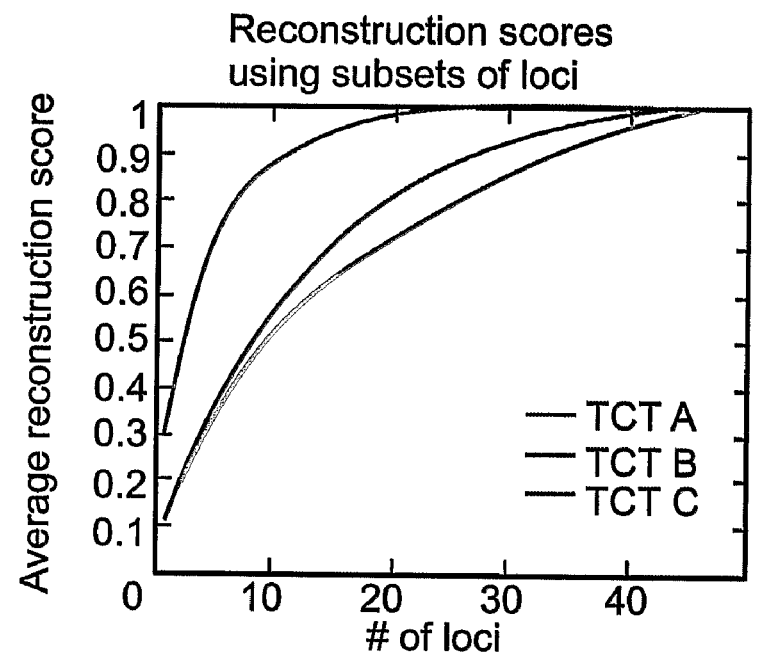
Figure 4F:
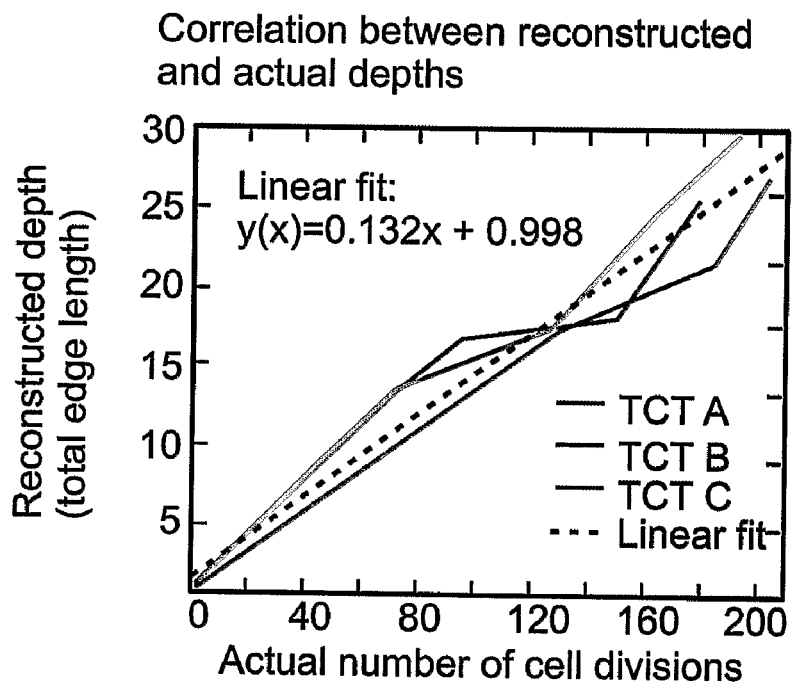
Figure 7:
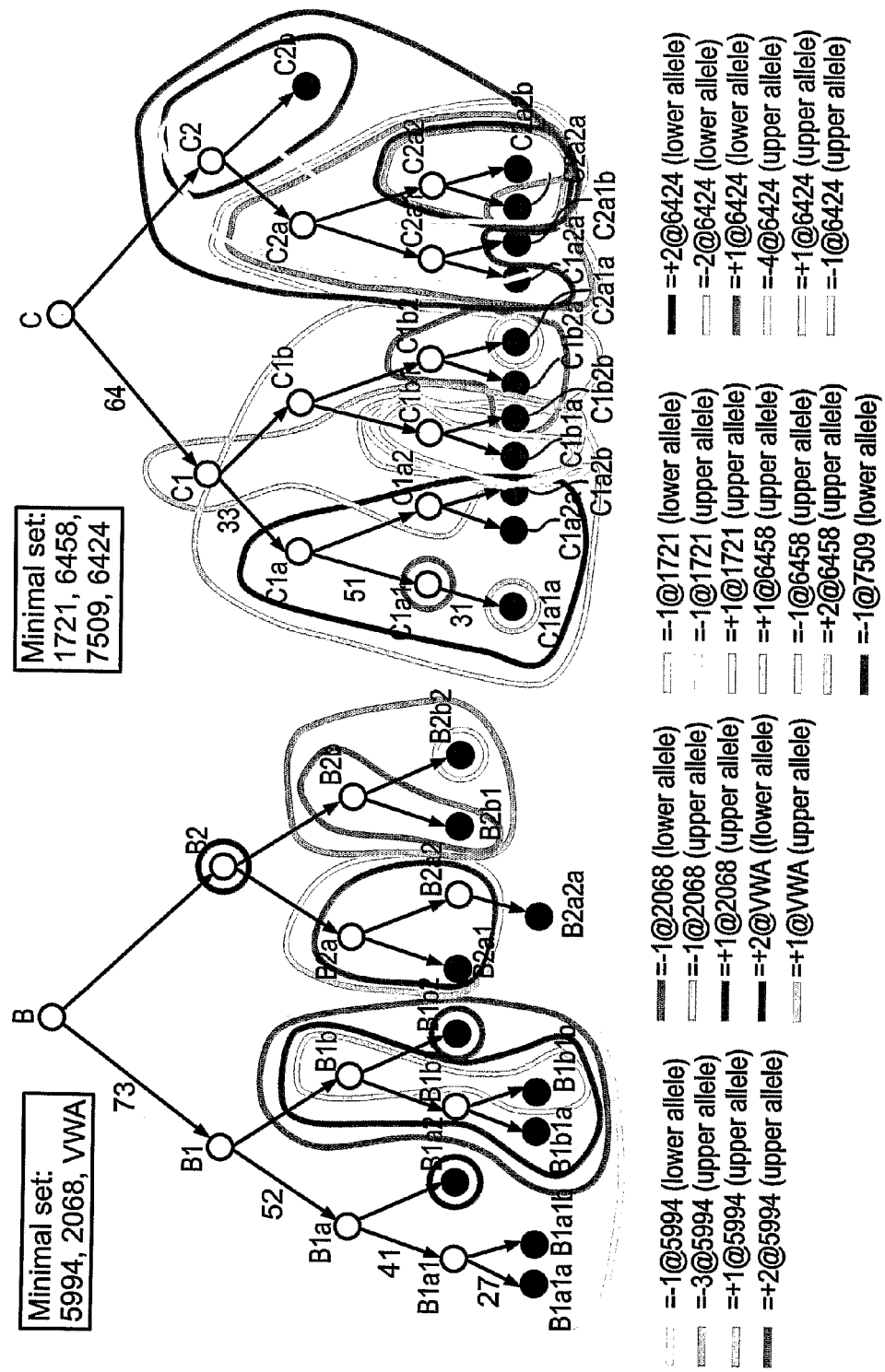
FIG. 7 is a diagrammatical model showing how minimal sets of loci yielded a perfect reconstruction of TCTs B and C. All reconstructions were performed using the neighbor-joining (NJ) phylogenetic algorithm with the 'equal or not' distance function, which is the sum of differing values between two identifiers. For TCT B at least 3 loci are required, and for TCT C at least 4 loci are required.
Figure 8:
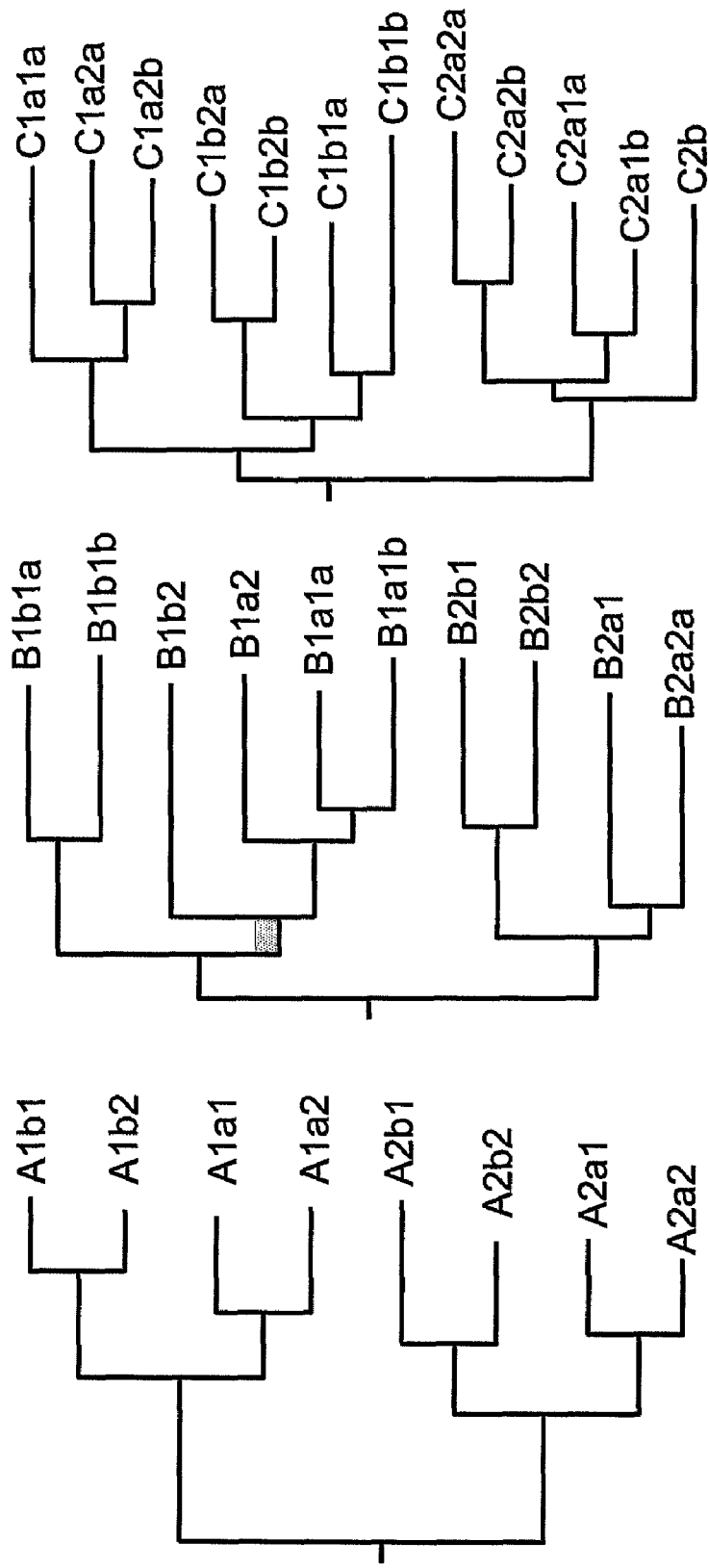
FIG. 8 is a set of diagrams showing reconstructed trees for TCTs A-C without using the root for reconstruction. All reconstructions were performed using NJ (with the 'equal or not' distance function). The unrooted trees outputted by NJ were rooted at the midpoint of the longest path from among all possible pathways between any two leaf nodes. Reconstructions of TCTs A and C are perfect, and a score of 7/8 was achieved for TCT B (red edge depicts the single topological mistake in the reconstruction of TCT B).

Tree reconstruction was performed as detailed above in Example 2. In all cases, the topology of the TCT was reconstructed precisely, thus the correct topology was found out of a total of (A) 135,135, (B) 34,459,425 and (C) 13,749,310,575 possible topologies for the 8, 10 and 12 leaves of TCTs A, B and C, respectively (FIG. 4b-d, insets). The edge length in the reconstructed trees were in linear correlation to the actual number of cell divisions in the TCTs (FIG. 4f; $R^2$=0.955). Furthermore, reconstructions of the TCTs without using the root identifiers (as detailed above), yielded perfect scores for TCTs A and C, and a score of 7/8 for TCT B, suggesting that accurate reconstruction is feasible from the extant cells alone (see FIG. 8). Finally, for each TCT, a minimal set of loci were found which yielded correct reconstruction using NJ (FIG. 4b, coloured contours, FIG. 7), and the number of loci needed were analyzed, on average, for precise reconstruction. It was found that TCT A, being simpler than trees B and C, indeed required fewer loci (FIG. 4e).

Thus tissue culture trees serve as a controlled system for phylogenetic analysis, and also may provide exact numerical data regarding rates, nature and correlation of mutations, allowing the assessment of the validity of MS mutation models.

Methods

Growth: LS174T human colon adenocarcinoma cells were obtained from the ECACC and were grown in medium containing EMEM (EBSS), 2 mM Glutamine, 1% Non Essential Amino Acids (NEAA), 10% Foetal Bovine Serum (FBS) and 1% Penicillin-Streptomycin.

Estimation of cell division rate: It was estimated that LS174T cells divide every 1.5 days according to the frequency of routine plate splits.

Creation of TCT edges: In each edge, cells were allowed to proliferate for the number of days expected to yield the number of cell divisions equal to the edge length (for more than 25 cell divisions plate splitting(s) were required).

Creation of cell clones: Clones from single cells were created by (i) trypsinizing and lifting cells from semi-confluent plates, (ii) thrusting the cells using a syringe ten times through a 1 μm mesh (A.D. Sinun; this step is necessary because LS174T cells grow in islands and tend to pile on top of each other), (iii) verifying that 99%+ of the cells are not attached to other cells, (iv) diluting the cells with ratios ranging between 1:5000 and 1:100,000 and [spreading] the cells on new plates, (v) waiting for single cells to form small islands (about 2-3 weeks), (vi) lifting islands to new plates using cloning cylinders (Sigma).

DNA extraction: DNA was extracted from clones of all cells corresponding to nodes of the TCTs using Wizard SV Genomic Purification System (Promega).

Cell freezing: Cells from all nodes of the TCTs were frozen in liquid nitrogen using a freezing medium containing 90% FBS and 10% DMSO.

Example 4

Preliminary In Vivo Experiments

*C. elegans*, with its known cell lineage tree, may provide an excellent in vivo control for the cell lineage inference procedure discussed above, except that its genome does not contain a sufficient number of MS to allow precise reconstruction. Hence, as a modest beginning, tissue samples from plants were chosen for analysis, initially avoiding the complex preparatory steps such as laser capture microdissection[42] and single-cell genome amplification[43], required for single-cell analysis. Plants are a good model system for lineage studies at the tissue level because of their nearly invariant pattern of cell division and lack of cell migration[44], which results in correlation between their physical and lineage distances. The first evidence supporting this correlation was obtained from analysis of MS variability in wild type *Robinia pseudoacacia* trees, which have been shown to have somatic mutations in an MS locus[45]. A tree was located with somatic MS variability and DNA was extracted from 28 tissue samples. Table 4 below displays the MS loci used for *Robinia pseudoacacia*

TABLE 4

| Locus # | Locus name | Repeat unit | SEQ ID NO: | Primers (5'->3') |
|---|---|---|---|---|
| 1 | Rops15 | CT | 103 | ROPS15F = CTAGATGCCCATTTTCAAGAATCC |
|  |  |  | 104 | ROPS15R = CGCAACTAGGGGCTAAATGAGG |
| 2 | Rops16 | CT | 105 | ROPS16F = AACCCTAAAAGCCTCGTTATC |
|  |  |  | 106 | ROPS16R = TGGCATTTTTTGGAAGACACC |

It was found that 25 samples contained the same genotype, which was considered normal, and three samples contained a mutant genotype. These three samples were physically clustered on the same small branch, which contained only mutant samples (FIG. 5e). This demonstrates that spontaneous somatic MS mutations in wild type plants can be used as clonal markers.

Analysis of multiple MS loci in *Robinia pseudoacacia* is not currently possible since its genome has not been sequenced, unlike *Arabidopsis thaliana*. Several clonal assays have previously been performed in *Arabidopsis* using genetic mutations that result in albino sectors on plant tissues[46,47]. Analysis of hundreds of plants with sectors showed that tissues from the same organ are more likely to be clonally related than tissues from different organs[46], and that samples which are separated by a small radial angle in the transverse plane are more likely to be clonally related than samples which are separated by a wide radial angle[47].

Instead of analyzing the phenotype of a large number of plants, each affected by a mutation in a single gene, one would hope to obtain a commensurate result by analyzing the genotype of a single plant using many mutations. For this purpose, an MMR-deficient *Arabidopsis* AtMSH2::TDNA mutant SALK_002708 [48] was grown (plant 4) and DNA was extracted from 23 different tissue samples (FIG. 5a).

Table 5 below displays the MS loci used for *Arabidopsis thaliana*.

TABLE 5

| Locus # | Locus name | Repeat unit | SEQ ID NO: | Primers (5'->3') |
|---|---|---|---|---|
| 1 | At5474 | AC | 107 | 5474F = TGTGCAGCTGGCTTCAAGACTC |
|   |        |    | 108 | 5474R = GAGTGCAATTACGTTCCCTGGAC |
| 2 | At2240 | AAG | 109 | 2240F = CCAACCATTAAGAATAAAGCAAGAACC |
|   |        |     | 110 | 2240R = CCATGCATATTTGCGGGCTTAC |
| 3 | At8907 | CTT | 111 | 8907F = TGTTGGTCACATGAGTGTCTCTGC |
|   |        |     | 112 | 8907R = CGAATCCAAAGGGAAAAGATGG |
| 4 | At3506 | CTT | 113 | 3506F = CATATTTGTGGTCCCTGGCTAATC |
|   |        |     | 114 | 3506R = CCACCAGTGACGAATTCCAAAAC |
| 5 | At5449 | CTT | 115 | 5449F = GCTTTATCCAACCTCCGATGACC |
|   |        |     | 116 | 5449R = GTCTTCGCAGACCATGTTGAGG |
| 6 | At7727 | AC | 117 | AT7727F = TGCACCCAAGAAATAGCATGGAC |
|   |        |    | 118 | AT7727R = CACGAGGGGAGTCCCTAGCAG |
| 7 | At8112 | AG | 119 | AT8112F = TCTCCCATCCGTTTGCTGAATC |
|   |        |    | 120 | AT8112R = TTGGTGTGCCAAAGTCAAACAAG |
| 8 | At7035 | AG | 121 | AT7035F = TGCTTCAAATGATTCAAATGTCTCG |
|   |        |    | 122 | AT7035R = TTAGATTAGATCGAGTGGGGAAACC |
| 9 | At7187 | AG | 123 | AT7187F = AAGCGCTCTTCATCTCATCATACC |
|   |        |    | 124 | AT7187R = CCACGTGGAAATCACCTTTACCTC |
| 10 | At4238 | AAG | 125 | 4238F = TTTGGAATTAGACGCGAAGCTG |
|    |        |     | 126 | 4238R = TGTTGATCGCCGTTTGATAAGC |
| 11 | At1495 | AAG | 127 | 1495F = GCCAAGACGCAGAAGAAGAGTTTG |
|    |        |     | 128 | 1495R = CCTTTTTGGCCTGTTGCTAACC |
| 12 | At3032 | AAG | 129 | AT3032F = TCTGTTGCCTTTTCTCATTGACATTC |
|    |        |     | 130 | AT3032R = GATTTAGGAGGGGCGAGAGTCC |
| 13 | At9608 | AAG | 131 | AT9608F = CTCCGGATCCCAAACCTTCAG |
|    |        |     | 132 | AT9608R = TGGGATGACAATGACGGAGAAG |
| 14 | At1810 | CTT | 133 | AT1810F = TGCGCTTCTTTTGTTAATTTGCAG |
|    |        |     | 134 | AT1810R = CCCGATTTTCTTGAAGCTTGCTC |
| 15 | At5445 | ATGT | 135 | AT5445F = ACAACGACTCAAAGAAGCAGAGAAG |
|    |        |      | 136 | AT5445R = CAACAACAAATTGGAGAGCCACAG |
| 16 | At3835 | AG | 137 | AT3835F = TGGAACTCAACGTGGATTGTGG |
|    |        |    | 138 | AT3835R = AGTTCAGGCGTTTGTTGCATGC |
| 17 | At4260 | AG | 139 | AT4260F = ATAGCTATTCCTACAAGGCATTTTGC |
|    |        |    | 140 | AT4260R = TCTCTTTGCGTTTTGGTATCCTG |
| 18 | At6446 | AG | 141 | AT6446F = TTCGAAGAAGAAGAAAGCAGAAGGAG |
|    |        |    | 142 | AT6446R = TTATCGCGGGCCAAAATTAACG |
| 19 | At3832 | AG | 143 | AT3832F = GCCTGAGTCAACTCGGCCATAAG |
|    |        |    | 144 | AT3832R = TACAACAAGTGGAGCGCGTGAG |
| 20 | At1471 | C | 145 | AT1471F = TCAACCGGAAAAGGACTGATTTC |
|    |        |   | 146 | AT1471R = GAAACTACCCCATACCGCATTCC |
| 21 | At1531 | CTT | 147 | AT1531F = GGGGTCCTGTCTTTTTGTTCTTATC |
|    |        |     | 148 | AT1531R = TGGTAAATTCTGAGCGTCCACAAC |
| 22 | At7063 | CTT | 149 | AT7063F = TTGGACCTGTCAAGTGTCAACAATC |
|    |        |     | 150 | AT7063R = CGCGTAACGTAGAGAGAATCTCAAAC |
| 23 | At6642 | AAG | 151 | AT6642F = TGAACCTCCGGCTCTTTGAGTC |
|    |        |     | 152 | AT6642R = CCCCTTCGTTCCAAACACTTAGC |

A scheme of the plant was created in which the position of each sample was recorded. Four categories of physical-radial distance between samples were defined (FIG. 5a,) as follows:

Samples from the same tertiary inflorescence were considered to have the smallest physical-radial distance, followed by samples from the same secondary (but not tertiary) inflorescence, samples from different but adjacent secondary inflorescences, and finally samples from distant secondary inflorescences, which were considered to have the largest physical-radial distance.

For each DNA sample 22 MS loci were amplified and a manual analysis of the amplification products was performed, yielding a set of sample identifiers. The full set of *Arabidopsis* identifiers is shown below in Table 6.

TABLE 6*

| | 8112 | 1810 | 3032 | 5445 | 7727 | 4238 | 5449 | 7187 | 2240 | 8907 | 5474 | 9608 |
|---|---|---|---|---|---|---|---|---|---|---|---|---|
| 1 | NaN | 0 | 0 | 0 | NaN | 0 | 0 | NaN | 0 | 0 | 0 | 0 |
| 2 | 0 | 0 | 0 | 0 | 0 | 0 | 0 | 0 | 0 | 0 | 0 | 0 |
| 3 | 0 | 0 | 0 | 0 | 0 | 0 | 0 | 0 | 0 | 0 | 0 | 0 |
| 4 | 0 | 0 | 0 | 0 | 0 | 0 | 0 | 0 | 0 | 0 | 0 | 0 |
| 5 | 0 | 0 | 0 | 0 | 0 | 0 | 0 | 0 | 0 | 0 | 0 | 0 |
| 6 | NaN | 0 | 0 | 0 | 0 | 0 | 0 | 0 | 1 | 0 | 0 | 0 |
| 7 | 0 | 0 | 0 | 0 | 0 | 0 | 0 | NaN | 0 | 0 | 0 | 0 |
| 8 | 0 | 0 | 0 | 0 | 0 | 0 | 0 | 0 | 0 | 0 | 0 | 0 |
| 9 | 0 | 0 | 0 | 0 | 0 | 0 | 0 | 0 | 0 | 0 | 0 | 0 |
| 10 | 0 | 0 | 0 | 0 | 0 | 0 | 0 | 0 | 0 | 0 | 0 | 0 |
| 11 | 1 | 0 | 0 | 0 | NaN | NaN | NaN | NaN | NaN | NaN | NaN | NaN |
| 12 | 1 | -1 | 0 | 0 | 0 | 0 | 0 | 0 | 0 | 0 | 0 | 0 |
| 13 | 1 | 0 | 0 | 0 | 0 | 0 | 0 | 0 | 0 | 0 | 0 | 0 |
| 14 | 1 | 0 | 0 | 0 | 0 | 0 | 0 | 0 | 0 | 0 | 0 | 0 |
| 15 | 1 | 0 | 0 | 0 | 0 | 0 | 0 | 0 | 0 | 0 | 0 | 0 |
| 16 | 1 | 0 | 0 | 0 | NaN | 0 | NaN | NaN | NaN | NaN | NaN | NaN |
| 17 | 0 | 0 | 0 | 0 | 0 | 0 | 0 | 0 | 0 | 0 | 0 | 0 |
| 18 | 0 | 0 | 0 | 0 | 0 | -1 | 0 | 0 | 0 | -1 | 0 | 0 |
| 19 | 0 | 0 | 0 | 0 | 0 | 0 | 0 | 0 | 1 | 0 | 0 | 0 |
| 20 | 0 | 0 | 0 | 0 | 0 | 0 | 0 | 0 | 1 | 0 | 0 | 0 |
| 21 | 0 | 0 | 0 | 0 | 0 | -1 | 0 | 0 | 0 | 0 | 0 | 0 |
| 22 | 0 | 0 | 0 | 0 | 0 | -1 | 0 | 0 | -1 | 0 | 0 | 0 |
| 23 | 0 | NaN | NaN | NaN | 0 | -1 | 0 | NaN | 0 | 0 | 0 | 0 |

| | 1495 | 7035 | 3506 | 3835 | 1471 | 4260 | 6446 | 7063 | 1531 | 3832 |
|---|---|---|---|---|---|---|---|---|---|---|
| 1 | 0 | NaN | 0 | 0 | 0 | 0 | -1 | 0 | 0 | 1 |
| 2 | 0 | 1 | 0 | 0 | NaN | 0 | 0 | NaN | NaN | 0 |
| 3 | 0 | 1 | 0 | 0 | NaN | 0 | 0 | NaN | NaN | 0 |
| 4 | 0 | 0 | 0 | 0 | NaN | 0 | 0 | NaN | NaN | NaN |
| 5 | 0 | 0 | 0 | NaN | NaN | 0 | 0 | NaN | NaN | NaN |
| 6 | 0 | 1 | 0 | 0 | NaN | NaN | 0 | NaN | NaN | 1 |
| 7 | 0 | 1 | 0 | 0 | 0 | 0 | 0 | 0 | 0 | 1 |
| 8 | 0 | 0 | 0 | 0 | 0 | 0 | 0 | 0 | 0 | 0 |
| 9 | 0 | 0 | 0 | 0 | NaN | 0 | 0 | 0 | 0 | 0 |
| 10 | 0 | 0 | 0 | 0 | NaN | 0 | 0 | 0 | 0 | 0 |
| 11 | NaN | NaN | NaN | 0 | 0 | 0 | 0 | 0 | 0 | NaN |
| 12 | 0 | 0 | 0 | NaN | NaN | NaN | NaN | NaN | NaN | NaN |
| 13 | 0 | 0 | 0 | 0 | NaN | 0 | 0 | 0 | 0 | 1 |
| 14 | 0 | 0 | 0 | 0 | 0 | 0 | 0 | 0 | 0 | 1 |
| 15 | 0 | 0 | 0 | 0 | -1 | -1 | 0 | 0 | 0 | 0 |
| 16 | NaN | NaN | NaN | 0 | 0 | -1 | 0 | 0 | 0 | 1 |
| 17 | 0 | 0 | 0 | 0 | 0 | -1 | 0 | 0 | 0 | NaN |
| 18 | 0 | -1 | 0 | 0 | NaN | -1 | 0 | 0 | 0 | 0 |
| 19 | 0 | 0 | 0 | 0 | 0 | -1 | 0 | 0 | 0 | 0 |
| 20 | 0 | 0 | 0 | 0 | 0 | -1 | 0 | 0 | 0 | 0 |
| 21 | 0 | -1 | 0 | 0 | 0 | -1 | 0 | 0 | 0 | NaN |
| 22 | 0 | -1 | 0 | 0 | -1 | -1 | 0 | 0 | 0 | NaN |
| 23 | 0 | NaN | 0 | 0 | 0 | -1 | 0 | 0 | 0 | NaN |

\* rows represent samples and columns represent loci; all values are relative to the "majority vote"; NaN represents un-amplified loci The identifiers were neither amenable to our automatic analysis nor could be used for lineage tree reconstruction since they represented tissue sample, each consisting of a heterogeneous population of cells, hence they were processed manually.

Information was extracted on somatic mutations in the plant by comparing the identifiers. For each locus the majority vote value (value shared by largest number of samples) was considered to be the base-line value, and different values were considered mutations. A total of 40 mutations in 17 samples were detected, of which 4 occurred in one sample only, and 36 occurred in two or more samples. The position of each of these shared mutations was marked in a transverse scheme of the plant (FIG. 5b), and analysis of this scheme revealed that shared mutations tend to be physically clustered. In order to quantify the correlation between physical and genetic distances in the plant tissues, the genetic distances were calculated between all of the identifiers (FIG. 5c), and compared to the physical-radial distances between the corresponding tissue samples. This comparison revealed a strong correlation (FIG. 5d), that is statistically significant for comparisons between all categories (p-values ranging from 0.00003-0.0248), except for between the first two (p=0.14).

In addition to this plant, experiments were performed on two other plants (plant #11, plant #12). In plant #11, DNA from 36 tissue samples was obtained, and the radial position of each sample was recorded. 23 MS loci were amplified for each DNA sample by PCR. A total of 17 mutations (relative to majority vote) were identified in 9 DNA samples in 6 MS loci. Each sample was assigned an identifier from the 23 amplified loci. Genetic distance between the samples was calculated by using the "equal or not" distance function, which is the sum of amplified loci with a different value between samples.

In plant # 12, DNA from 47 tissue samples was obtained, and the radial position of each sample was recorded. 23 MS loci were amplified for each DNA sample by PCR. A total of 19 mutations (relative to majority vote) were identified in 19 DNA samples in a single MS locus. Each sample was assigned an identifier from the 23 amplified loci. Genetic distance between the samples was calculated by using the "equal or not" distance function.

Data from plants #11 and #12 were combined and the genetic distances were plotted (using Excel software) against the radial distances. A positive trend was observed in the plot and a linear fit of the plot produced a coefficient of 0.0006 and a $R^2$ value of 0.0036.

Thus, the analysis of two other *Arabidopsis* plants found many fewer somatic mutations and a weak correlation between genetic and radial distances.

Methods

Growth: *Arabidopsis* AtMSH2::TDNA mutant SALK_002708 (seeds kindly provided by J. Leonard) were grown in a growth room in long day conditions.

Strain verification: all *Arabidopsis* plants were verified as mutant as described in [47] (data not shown).

DNA extraction: DNA was extracted from *Arabidopsis* and *Robinia* samples using the Extract-N-Amp kit (Sigma).

Sample orientations of *Arabidopsis* plant No. 4: the plant was photographed from different angles and the radial positions of the samples were obtained from analysis of the photos Example 5

Iterative Cell-Depth Analysis

Figure 9:
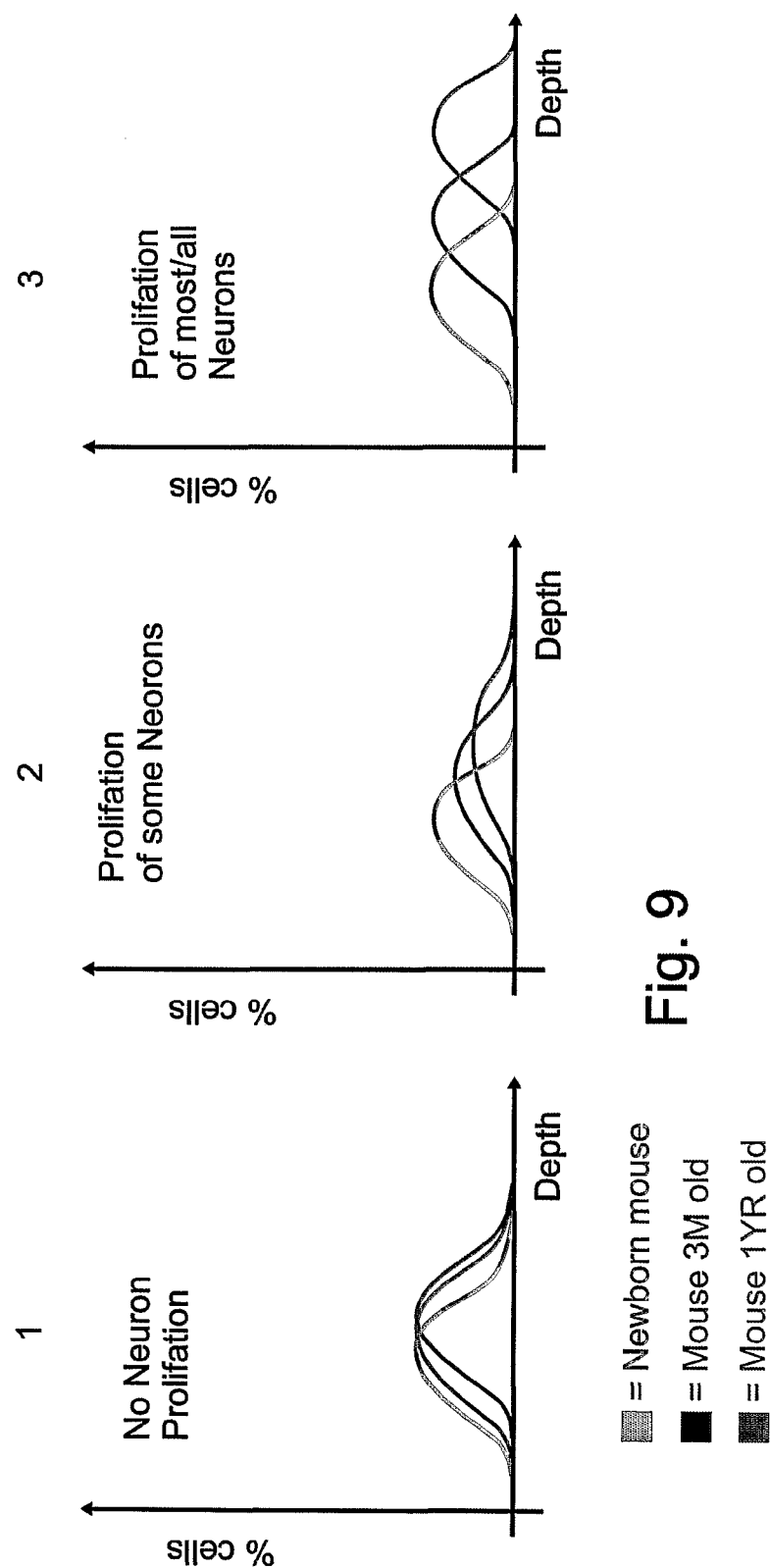
FIG. 9 is an illustration of depth histograms effected on neurons of mice of different ages.

Iterative depth analysis (as described above) may be effected in a number of tissues of an individual or in a number of individuals, requiring an approximately constant mutation rate in the examined tissues. Depth analysis is effected on histograms rather than on lineage trees. For example (see FIG. 9), by performing depth analysis on neuronal tissue samples at various developmental stages one can obtain valuable information regarding the growth dynamics of neurons. For example, one can deduce whether there is post-natal neuronal proliferation, or whether there is neuronal regeneration following injury. Essentially, if cell depth distribution is substantially identical in all samples, no neuronal generation is suggested. Inversely, if cell depth distribution varies, neuronal generation may be inferred.

Example 6

Identifying the Origin of Cancers of Unknown Primary Site

In most metastases, the primary cancer site is known or can be diagnosed, mainly based on the body part in which metastastic cells are found and the type of these cells. In some cases, the site of origin of metastases cannot be identified, and such cancers are diagnosed as carcinomas of unknown primary (CUP).

Today, the definition of CUP includes patients with histologically confirmed metastatic cancer in whom a detailed medical history, a complete physical examination, including a pelvic and rectal examination, full blood count and biochemistry, urinalysis and stool occult blood testing, histopathological review of biopsy material with the use of immunohistochemistry, chest radiography, computed tomography of abdomen and pelvis, and in certain cases mammography, fail to identify the primary site [Pavlidis N. (2003) *Ann Oncol.* 14 Suppl 3:iii11-8].

Epidemiology. CUP accounts for approximately 3% of all malignant neoplasms, representing the seventh to eighth most frequent type of cancer and the fourth commonest cause of cancer death in both males and females [Pavlidis N. (2003) *Ann Oncol.* 14 Suppl 3:iii11-8]. Even with an extensive diagnostic work-up using modern pathological and imaging procedures, the frequency of detection of the primary tumor site remains low. Less than 20% of CUP patients have a primary site identified antemortem, while almost 70% of autopsied cases remain undiagnosed [Pavlidis N. (2003) *Ann Oncol.* 14 Suppl 3:iii11-8].

Possible tissues of origin: Studies suggest that unknown primary cancers often start in the lungs or pancreas, and less often in the colon, rectum, breast, or prostate [National Cancer Institute—Cancer Facts (cis.nci.nih.gov/fact/6_19.htm), Reynolds T. Head Neck. 2003 June; 25(6):499-504]. The original tumor may lurk in the body, too small to be found, or may have been destroyed via immune surveillance by the time its deadly offshoots reach critical mass [Reynolds T. Head Neck. 2003 June; 25(6):499-504].

The importance of identifying the origins of tumors: Identifying the primary tumor site is important because knowing its location and type often helps doctors plan the best treatment [Ayoub J. M., Hubbard K. P. & Lenzi R—*Unknown primary carcinomas: diagnosis and management* (from Medical Oncology: a comprehensive review)]. Treatment that is specific to the suspected type of cancer is likely to be more effective [Ayoub J. M., Hubbard K. P. & Lenzi R—*Unknown primary carcinomas: diagnosis and management* (from Medical Oncology: a comprehensive review)], and the majority of CUPs remain relatively unresponsive to systemic therapy [Pavlidis N. (2003) *Ann Oncol.* 14 Suppl 3:iii11-8]. Currently, treatment has been poor for many of the patients, and their median of survival time is about 4-5 months [Greco F A, Burris H A 3rd, Erland J B, Gray J R, Kalman L A, Schreeder M T, Hainsworth J D. Cancer. 2000 Dec. 15; 89(12):2655-60].

Figure 11B:
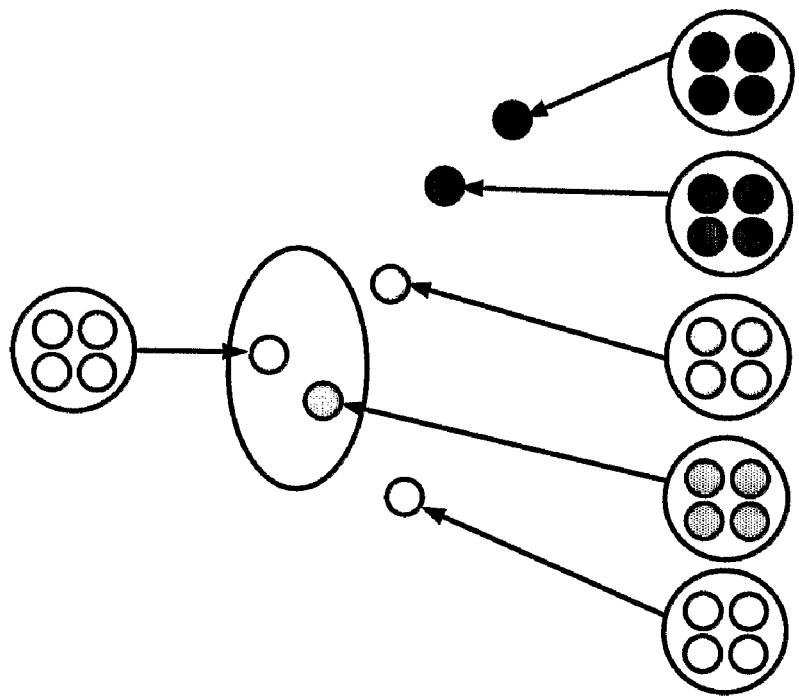
FIGS. 11a-b are schematic illustrations depicting identification of tumor origin using the teachings of the present invention.
Figure 11A:
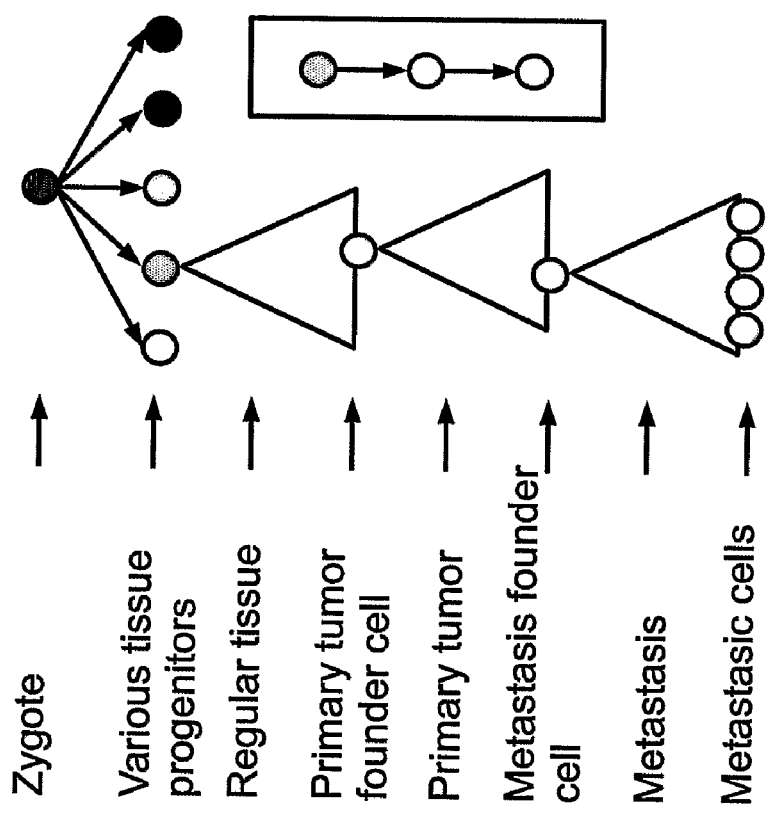

Identifying tumor origin from DNA of metastases: The following is suggested for identifying the origin of tumors from the DNA sequences of metastases originating from these tumors. The following sequence of events is suggested (FIG. 11): the zygote gives rise to progenitor cells, from which the various tissues are derived. A primary tumor originates from a single cell in one of these tissues, and after some clonal expansion, a metastasis originates from a single cell from the primary tumor. Identification of the tumor origin tissue is performed by (FIG. 11*b*): (i) taking samples from the cancerous tissue and from potential tissues of origin; (ii) deriving the cellular identifier (genotypic marker or representation thereof) (CI) of the progenitor cell of each tissue based on the CIs of sampled cells; (iii) computing distances between the CI of the cancerous tissue and the CI of the progenitors of potential origin tissues; (iv) if one distance is significantly closer than others, output the corresponding tissue as assumed tissue of origin. The motivation of this method is that the mutational drift is proportional to lineage distances; hence the distance between the cellular identifier of the founder cell of the metastasis is expected to be closest to the cellular identifier of the founder cell of the tissue from which it originated.

Proof of concept experiment. Analysis is performed on cancerous tissue samples obtained either from MMR-deficient mice (hMLH1—[Delmann W., Cohen P. E., Kane M., Lau K., Morrow B., Bennett S., Umar A., Kunkel T., Cattoretti G., Chaganti R., Pollard J. W., Kolodner R. D. & Kucherlapati R. (1996) Cell 85(7):1125-34], obtained from the MMHCC repository) or from human autopsies. DNA is obtained from the metastasis and from various potential tissues of origin (lungs, pancreas, colon, rectum, etc.), and the corresponding CIs are derived. It is important to state that the topology of the cellular lineage tree (including the tumor and metastasis) affects the number of microsatellites which are necessary to perform good analysis. Note, that if the number of cell divisions between the zygote and the tissue progenitors is small relatively to the number of cell divisions between the progenitor of the origin tissue of the cancer and the progenitor of the metastasis, analysis may be difficult, and a large MS set may be necessary.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

REFERENCES

Cited by Numerals

Other References are Cited in the Application

1. Sulston, J. E., Schierenberg, E., White, J. G. & Thomson, J. N. The embryonic cell lineage of the nematode *Caenorhabditis elegans*. Dev Biol 100, 64-119 (1983).
2. Stern, C. D. & Fraser, S. E. Tracing the lineage of tracing cell lineages. Nat Cell Biol 3, E216-8 (2001).
3. Clarke, J. D. & Tickle, C. Fate maps old and new. Nat Cell Biol 1, E103-9 (1999).
4. Noctor, S. C., Flint, A. C., Weissman, T. A., Dammerman, R. S. & Kriegstein, A. R. Neurons derived from radial glial cells establish radial units in neocortex. Nature 409, 714-20 (2001).
5. Ardavin, C. et al. Origin and differentiation of dendritic cells. Trends Immunol 22, 691-700 (2001).
6. Anderson, D. J., Gage, F. H. & Weissman, I. L. Can stem cells cross lineage boundaries? Nat Med 7, 393-5 (2001).
7. Kim, K. M. & Shibata, D. Methylation reveals a niche: stem cell succession in human colon crypts. Oncogene 21, 5441-9 (2002).
8. Dor, Y., Brown, J., Martinez, O. I & Melton, D. A. Adult pancreatic beta-cells are formed by self-duplication rather than stem-cell differentiation. Nature 429, 41-6 (2004).
9. Alvarez-Buylla, A., Garcia-Verdugo, J. M. & Tramontin, A. D. A unified hypothesis on the lineage of neural stem cells. Nat Rev Neurosci 2, 287-93 (2001).
10. Walsh, C. & Cepko, C. L. Widespread dispersion of neuronal clones across functional regions of the cerebral cortex. Science 255, 434-40 (1992).
11. Bernards, R. & Weinberg, R. A. A progression puzzle. Nature 418, 823 (2002).
12. Yamamoto, N. et al. Determination of clonality of metastasis by cell-specific color-coded fluorescent-protein imaging. Cancer Res 63, 7785-90 (2003).
13. Hope, K. J., Jin, L. & Dick, J. E. Acute myeloid leukemia originates from a hierarchy of leukemic stem cell classes that differ in self-renewal capacity. Nat Immunol 5, 738-43 (2004).
14. Weigelt, B. et al. Gene expression profiles of primary breast tumors maintained in distant metastases. Proc Natl Acad Sci USA 100, 15901-5 (2003).
15. Tang, M. et al. Microsatellite analysis of synchronous and metachronous tumors: a tool for double primary tumor and metastasis assessment. Diagn Mol Pathol 12, 151-9 (2003).
16. Ben-Yair, R., Kahane, N. & Kalcheim, C. Coherent development of dermomyotome and dermis from the entire mediolateral extent of the dorsal somite. Development 130, 4325-36 (2003).
17. Zernicka-Goetz, M. et al. Following cell fate in the living mouse embryo. Development 124, 1133-7 (1997).
18. Dubertret, B. et al. In vivo imaging of quantum dots encapsulated in phospholipid micelles. Science 298, 1759-62 (2002).
19. Shelley Hwang, E. et al. Clonality of lobular carcinoma in situ and synchronous invasive lobular carcinoma. Cancer 15, 2562-72 (2004).
20. Parrella, P. Detection of mitochondrial DNA mutations in primary breast cancer and fine-needle aspirates. Cancer Res 61, 7623-6 (2001).
21. van Dongen, J. J. et al. Design and standardization of PCR primers and protocols for detection of clonal immunoglobulin and T-cell receptor gene recombinations in suspect lymphoproliferations: report of the BIOMED-2 Concerted Action BMH4-CT98-3936. Leukemia 17, 2257-317 (2003).
22. Tan, S. S. et al. Cell dispersion patterns in different cortical regions studied with an X-inactivated transgenic marker. Development 121, 1029-39 (1995).
23. Fujii, H. et al. Genetics of synchronous uterine and ovarian endometrioid carcinoma: combined analyses of loss of heterozygosity, PTEN mutation, and microsatellite instability. Hum Pathol 33, 421-8 (2002).
24. Morandi, L. et al. Intraepidermal cells of Paget's carcinoma of the breast can be genetically different from those of the underlying carcinoma. Hum Pathol 34, 1321-30 (2003).
25. Tsao, J. L. et al. Colorectal adenoma and cancer divergence. Evidence of multilineage progression. Am J Pathol 154, 1815-24 (1999).
26. Buermeyer, A. B., Deschenes, S. M., Baker, S. M. & Liskay, R. M. Mammalian DNA mismatch repair. Annu Rev Genet. 33, 533-64 (1999).
27. Gilbert, S. *Developmental Biology*, 6th edition (Sinauer Ass., Sunderland, 2000).
28. Graur, D. & Wen-Hsiung, L. *Fundamentals of molecular evolution*, 2nd edition (Sinauer Ass., Sunderland, 2000).
29. Brown, J. R., Douady, C. J., Italia, M. J., Marshall, W. E. & Stanhope, M. J. Universal trees based on large combined protein sequence data sets. Nat Genet 28, 281-5 (2001).
30. Ellegren, H. Microsatellites: simple sequences with complex evolution Nat Rev Genet 5, 435-45 (2004).
31. Vilkki, S. et al. Extensive somatic microsatellite mutations in normal human tissue. Cancer Res 61, 4541-4 (2001).
32. Wei, K., Kucherlapati, R. & Edelmann, W. Mouse models for human DNA mismatch-repair gene defects Trends Mol Med 8, 346-53 (2002).
33. Hearne, C. M., Ghosh, S. & Todd, J. A. Microsatellites for linkage analysis of genetic traits. Trends Genet. 8, 288-94 (1992).

34. Butler, J. (2001), *Forensic DNA Typing*, Academic Press
35. Schlotterer, C. Genealogical inference of closely related species based on microsatellites. Genet Res. 78, 209-12 (2001).
36. Bowcock, A. M. High resolution of human evolutionary trees with polymorphic microsatellites. Nature 368, 455-7 (1994).
37. Shinde, D., Lai, Y., Sun, F. & Arnheim, N. Taq DNA polymerase slippage mutation rates measured by PCR and quasi-likelihood analysis: (CA/GT)n and (A/T)n microsatellites. Nucleic Acids Res. 31, 974-80 (2003).
38. Brinkmann, B., Klintschar, M., Neuhuber, F., Huhne, J. & Rolf, B. Mutation rate in human microsatellites: influence of the structure and length of the tandem repeat. Am J Hum Genet 62, 1408-15 (1998).
39. Snabes, M. C. et al. Preimplantation single-cell analysis of multiple genetic loci by whole-genome amplification. Proc Natl Acad Sci USA. 91, 6181-5 (1994).
40. Deng, G., Chen, A., Hong, J., Chae, H. S. & Kim, Y. S. Methylation of CpG in a small region of the hMLH1 promoter invariably correlates with the absence of gene expression. Cancer Res 59, 2029-33 (1999).
41. Shibata, D., Peinado, M. A., Ionov, Y., Malkhosyan, S. & Perucho, M. Genomic instability in repeated sequences is an early somatic event in colorectal tumorigenesis that persists after transformation. Nat Genet 6, 273-81 (1994).
42. Emmert-Buck, M. R. et al. Laser capture microdissection. Science 274, 998-1001 (1996).
43. Wells, D., Sherlock, J. K., Handyside, A. H. & Delhanty, J. D. Detailed chromosomal and molecular genetic analysis of single cells by whole genome amplification and comparative genomic hybridisation. Nucleic Acids Res. 27, 1214-8 (1999).
44. Meyerowitz, E. M. and Somerville, C. R. (1994), *Arabidopsis*. Cold Spring Harbor Laboratory Press: New York (p. 299)
45. Lian, C., Oishi, R., Miyashita, N. & Hogetsu, T. High somatic instability of a microsatellite locus in a clonal tree, *Robinia pseudoacacia*. Theor Appl Genet. 108, 836-41 (2004).
46. Woodrick, R., Martin, P. R., Birman, I. & Pickett, F. B. The *Arabidopsis* embryonic shoot fate map. Development 127, 813-20 (2000).
47. Furner, I. J. & Pumfrey, J. E. Cell fate in the shoot apical meristem of *Arabidopsis thaliana*. Development 115, 755-764 (1992).
48. Leonard, J. M., Bollmann, S. R. & Hays, J. B. Reduction of stability of *arabidopsis* genomic and transgenic DNA-repeat sequences (microsatellites) by inactivation of AtMSH2 mismatch-repair function. Plant Physiol 133, 328-38 (2003).
49. Hood, L. & Galas, D. The digital code of DNA. Nature 421, 444-8 (2003).

What is claimed is:

1. A method of assessing clonality of a neoplasm in an individual, the method comprising:
    (a) obtaining a cell sample of the neoplasm of the individual;
    (b) determining at least one genotypic marker for each cell of said cell sample of the neoplasm; and
    (c) computationally clustering data representing said at least one genotypic marker and additional genotypic markers of a plurality of cells, to thereby assess clonality of the neoplasm in the individual.

2. The method of claim 1, wherein said genotypic marker is a cell division marker.

3. The method of claim 1, wherein said genotypic marker exhibits somatic variability.

4. The method of claim 3, wherein said genotypic marker exhibiting somatic variability is a repetitive sequence element.

5. The method of claim 1, wherein said clustering is effected by a clustering algorithm.

6. The method of claim 1, wherein the neoplasm is of a blood forming tissue.

7. The method of claim 1, wherein the neoplasm is a cancer of unknown primary tumor.

* * * * *

```
SEQUENCE LISTING

<160> NUMBER OF SEQ ID NOS: 152

<210> SEQ ID NO 1
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 1
gggccttctt atattgcttc                                                    20

<210> SEQ ID NO 2
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 2
ggaaagactg gaccaaagag                                                    20

<210> SEQ ID NO 3
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 3
ctgggaagtt caagtggctg tg                                                 22

<210> SEQ ID NO 4
<211> LENGTH: 21
<212> TYPE: DNA
<213> ORGANISM: Artificial sequence
<220> FEATURE:
```

-continued

<223> OTHER INFORMATION: Single strand DNA oligonucleotide

<400> SEQUENCE: 4
atcactgcct ggaagcgaca c                                              21

<210> SEQ ID NO 5
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 5
agctaactac tctccaccca tac                                            23

<210> SEQ ID NO 6
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 6
ccatgctaag tttatgatgt ctg                                            23

<210> SEQ ID NO 7
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 7
ttccccaatc tcaccgtcac tc                                             22

<210> SEQ ID NO 8
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 8
ggcctagcac ctcaccttttt cc                                            22

<210> SEQ ID NO 9
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 9
atcatgcaga ccctgcctca ag                                             22

<210> SEQ ID NO 10
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 10
actgtggcat ctcccctagc ag                                             22

<210> SEQ ID NO 11

```
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 11
ggagcagagg aggtggcaga ag                                              22

<210> SEQ ID NO 12
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 12
acacttggac agcatttcct gtgtc                                           25

<210> SEQ ID NO 13
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 13
ttgccagaac attaagttag aatttgc                                         27

<210> SEQ ID NO 14
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 14
tttgccctct agcattttc acc                                              23

<210> SEQ ID NO 15
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 15
acaaaaagcc ccaggggtta agt                                             23

<210> SEQ ID NO 16
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 16
accatttagc gtttgtgtgt gcat                                            24

<210> SEQ ID NO 17
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 17
```

```
tgcgggtcag aaaacaagtc tc                                              22

<210> SEQ ID NO 18
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 18
ctgtctagcc cattcctgtt gac                                             23

<210> SEQ ID NO 19
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 19
ttttcacttg atcctgcacc aatc                                            24

<210> SEQ ID NO 20
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 20
ttccactttt gcccagagat aac                                             23

<210> SEQ ID NO 21
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 21
agctgcttac cacgaatgtc                                                 20

<210> SEQ ID NO 22
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 22
tcagactttg agccctgcta                                                 20

<210> SEQ ID NO 23
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 23
agctagtctg gcatgagcag                                                 20

<210> SEQ ID NO 24
<211> LENGTH: 20
<212> TYPE: DNA
<213> ORGANISM: Artificial sequence
<220> FEATURE:
```

<223> OTHER INFORMATION: Single strand DNA oligonucleotide

<400> SEQUENCE: 24
ctatcccctg atgatctccc                                                    20

<210> SEQ ID NO 25
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 25
gtcagtgctc aggctgaact gc                                                 22

<210> SEQ ID NO 26
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 26
tctgcctcct ccattccgtt ac                                                 22

<210> SEQ ID NO 27
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 27
cggttacaag ctccacagca atc                                                23

<210> SEQ ID NO 28
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 28
tgacacagag agggaatcct cgtag                                              25

<210> SEQ ID NO 29
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 29
tgggtcacat cctaccaacc ac                                                 22

<210> SEQ ID NO 30
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 30
aggccaacaa gcaaaatcaa gg                                                 22

<210> SEQ ID NO 31

```
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 31
cctttccatg tttgctcgct tg                                          22

<210> SEQ ID NO 32
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 32
cccactcaat cctgatgaat gacc                                        24

<210> SEQ ID NO 33
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 33
caccgctggc agttcttttc                                             20

<210> SEQ ID NO 34
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 34
agcaaagaca aggttaagaa tcacg                                       25

<210> SEQ ID NO 35
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 35
tgagatggga gaagggagaa tcac                                        24

<210> SEQ ID NO 36
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 36
ggcgctttcc agttactgtt tg                                          22

<210> SEQ ID NO 37
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 37
```

```
cctggttctt gctatggcaa atg                                             23

<210> SEQ ID NO 38
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 38
ctaatctgct cctcacacta cac                                             23

<210> SEQ ID NO 39
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 39
gctggtgcag gaacagttgg                                                 20

<210> SEQ ID NO 40
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 40
ggctgctctg gctttaagtt cc                                              22

<210> SEQ ID NO 41
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 41
cgcacacggg caagagtaag ac                                              22

<210> SEQ ID NO 42
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 42
aggattcggg tggggcaag g                                                21

<210> SEQ ID NO 43
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 43
gcatccctag atacagtttg gc                                              22

<210> SEQ ID NO 44
<211> LENGTH: 23
<212> TYPE: DNA
<213> ORGANISM: Artificial sequence
<220> FEATURE:
```

<223> OTHER INFORMATION: Single strand DNA oligonucleotide

<400> SEQUENCE: 44
gccaacttag aaaacagcag ggc                                          23

<210> SEQ ID NO 45
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 45
cacagcctgg gagacaagag tg                                           22

<210> SEQ ID NO 46
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 46
tgccatcagt agaagcatga gg                                           22

<210> SEQ ID NO 47
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 47
gaggctgcag ctgctattca aag                                          23

<210> SEQ ID NO 48
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 48
caatgccatt cctgccatct c                                            21

<210> SEQ ID NO 49
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 49
ggaggtgctc agccatattt gc                                           22

<210> SEQ ID NO 50
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 50
tgacagctct acaccgaatt atttgc                                       26

<210> SEQ ID NO 51

```
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 51
gaaagaccag atatggtttg ccttc                                           25

<210> SEQ ID NO 52
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 52
agcaatccgg gaacacttca tc                                              22

<210> SEQ ID NO 53
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 53
gagccatgtt catgccactg                                                 20

<210> SEQ ID NO 54
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 54
caaacccgac taccagcaac                                                 20

<210> SEQ ID NO 55
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 55
ctgggagtca gaagttgcaa tg                                              22

<210> SEQ ID NO 56
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 56
gcctcatctc ctgtcctgca c                                               21

<210> SEQ ID NO 57
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 57
```

```
gccaaggcag gaagatcact tg                                              22

<210> SEQ ID NO 58
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 58
ccctttcttc cacacaccca tc                                              22

<210> SEQ ID NO 59
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 59
cccagaccaa gaaccaactt gc                                              22

<210> SEQ ID NO 60
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 60
atatggtccg ggatgcaaat g                                               21

<210> SEQ ID NO 61
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 61
agggatattc agcccgaggt g                                               21

<210> SEQ ID NO 62
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 62
actgccactc cttgccccat tc                                              22

<210> SEQ ID NO 63
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 63
aaattgggcc agtggtttat cc                                              22

<210> SEQ ID NO 64
<211> LENGTH: 22
<212> TYPE: DNA
<213> ORGANISM: Artificial sequence
<220> FEATURE:
```

```
<223> OTHER INFORMATION: Single strand DNA oligonucleotide

<400> SEQUENCE: 64
ccactggggt gtgtgtgtgt ag                                          22

<210> SEQ ID NO 65
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 65
gggcagtcgc tacaaaggtt tc                                          22

<210> SEQ ID NO 66
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 66
tgatggcttc tgattacata ttccttg                                     27

<210> SEQ ID NO 67
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 67
gcaacaagag tgaagctcct tctcag                                      26

<210> SEQ ID NO 68
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 68
gtccgtgatc tgcccgcttc                                             20

<210> SEQ ID NO 69
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 69
aattgccatt gcaaccacat tg                                          22

<210> SEQ ID NO 70
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 70
tggcaccagt gagggtctta ttg                                         23

<210> SEQ ID NO 71
```

```
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 71
aatcctttga acccaggagg                                              20

<210> SEQ ID NO 72
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 72
gagggtttgg tgtgtgttag tattc                                        25

<210> SEQ ID NO 73
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 73
agcagcttgg atcactggtg tg                                           22

<210> SEQ ID NO 74
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 74
aatctggagg cgaaaattgc ag                                           22

<210> SEQ ID NO 75
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 75
ccgtctccac caaaaccagt c                                            21

<210> SEQ ID NO 76
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 76
acccaacacc ctgctgcttc                                              20

<210> SEQ ID NO 77
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 77
```

-continued cttgaacccg ggaggtggag                                               20

<210> SEQ ID NO 78
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 78
ggctcattaa ggaccttttg gg                                            22

<210> SEQ ID NO 79
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 79
atatgtgagt caattcccca ag                                            22

<210> SEQ ID NO 80
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 80
tgtattagtc aatgttctcc ag                                            22

<210> SEQ ID NO 81
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 81
attaacttcc tacaccacaa c                                             21

<210> SEQ ID NO 82
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 82
gtagagcaag accaccttg                                                19

<210> SEQ ID NO 83
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 83
gccccatagg ttttgaactc a                                             21

<210> SEQ ID NO 84
<211> LENGTH: 22
<212> TYPE: DNA
<213> ORGANISM: Artificial sequence
<220> FEATURE:

<223> OTHER INFORMATION: Single strand DNA oligonucleotide

<400> SEQUENCE: 84
tgatttgtct gtaattgcca gc                                              22

<210> SEQ ID NO 85
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 85
tttttgtatt tcatgtgtac attcg                                           25

<210> SEQ ID NO 86
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 86
cgtagctata attagttcat tttca                                           25

<210> SEQ ID NO 87
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 87
acagaagtct gggatgtgga                                                 20

<210> SEQ ID NO 88
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 88
gcccaaaaag acagacagaa                                                 20

<210> SEQ ID NO 89
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 89
ccctagtgga tgataagaat aatcagtatg                                      30

<210> SEQ ID NO 90
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 90
ggacagatga taaatacata ggatggatgg                                      30

<210> SEQ ID NO 91

```
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 91
tgtcatagtt tagaacgaac taacg                                         25

<210> SEQ ID NO 92
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 92
ctgaggtatc aaaaactcag agg                                           23

<210> SEQ ID NO 93
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 93
gggtgatttt cctctttggt                                               20

<210> SEQ ID NO 94
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 94
tgattccaat catagccaca                                               20

<210> SEQ ID NO 95
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 95
cactagcacc cagaaccgtc                                               20

<210> SEQ ID NO 96
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 96
ccttgtcagc gtttatttgc c                                             21

<210> SEQ ID NO 97
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 97
```

```
gtgggctgaa aagctcccga ttat                                          24

<210> SEQ ID NO 98
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 98
attcaaaggg tatctgggct ctgg                                          24

<210> SEQ ID NO 99
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 99
actgcagtcc aatctgggt                                                19

<210> SEQ ID NO 100
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 100
atgaaatcaa cagaggcttg                                               20

<210> SEQ ID NO 101
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 101
tcacacagct gttaagtggc agag                                          24

<210> SEQ ID NO 102
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 102
catgccctgt tccctgctaa ag                                            22

<210> SEQ ID NO 103
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 103
ctagatgccc attttcaaga atcc                                          24

<210> SEQ ID NO 104
<211> LENGTH: 22
<212> TYPE: DNA
<213> ORGANISM: Artificial sequence
<220> FEATURE:
```

<223> OTHER INFORMATION: Single strand DNA oligonucleotide

<400> SEQUENCE: 104
cgcaactagg ggctaaatga gg                                        22

<210> SEQ ID NO 105
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 105
aaccctaaaa gcctcgttat c                                         21

<210> SEQ ID NO 106
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 106
tggcattttt tggaagacac c                                         21

<210> SEQ ID NO 107
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 107
tgtgcagctg gcttcaagac tc                                        22

<210> SEQ ID NO 108
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 108
gagtgcaatt acgttccctg gac                                       23

<210> SEQ ID NO 109
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 109
ccaaccatta agaataaagc aagaacc                                   27

<210> SEQ ID NO 110
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 110
ccatgcatat ttgcgggctt ac                                        22

<210> SEQ ID NO 111

```
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 111
tgttggtcac atgagtgtct ctgc                                        24

<210> SEQ ID NO 112
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 112
cgaatccaaa gggaaaagat gg                                          22

<210> SEQ ID NO 113
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 113
catatttgtg gtccctggct aatc                                        24

<210> SEQ ID NO 114
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 114
ccaccagtga cgaattccaa aac                                         23

<210> SEQ ID NO 115
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 115
gctttatcca acctccgatg acc                                         23

<210> SEQ ID NO 116
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 116
gtcttcgcag accatgttga gg                                          22

<210> SEQ ID NO 117
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 117
```
tgcacccaag aaatagcatg gac                            23

<210> SEQ ID NO 118
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 118
cacgagggga gtccctagca g                              21

<210> SEQ ID NO 119
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 119
tctcccatcc gtttgctgaa tc                             22

<210> SEQ ID NO 120
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 120
ttggtgtgcc aaagtcaaac aag                            23

<210> SEQ ID NO 121
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 121
tgcttcaaat gattcaaatg tctcg                          25

<210> SEQ ID NO 122
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 122
ttagattaga tcgagtgggg aaacc                          25

<210> SEQ ID NO 123
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 123
aagcgctctt catctcatca tacc                           24

<210> SEQ ID NO 124
<211> LENGTH: 24
<212> TYPE: DNA
<213> ORGANISM: Artificial sequence
<220> FEATURE:

<223> OTHER INFORMATION: Single strand DNA oligonucleotide

<400> SEQUENCE: 124
ccacgtggaa atcaccttta cctc                                      24

<210> SEQ ID NO 125
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 125
tttggaatta gacgcgaagc tg                                        22

<210> SEQ ID NO 126
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 126
tgttgatcgc cgtttgataa gc                                        22

<210> SEQ ID NO 127
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 127
gccaagacgc agaagaagag tttg                                      24

<210> SEQ ID NO 128
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 128 ccttttggc ctgttgctaa cc                                         22

<210> SEQ ID NO 129
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 129
tctgttgcct tttctcattg acattc                                    26

<210> SEQ ID NO 130
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 130
gatttaggag gggcgagagt cc                                        22

<210> SEQ ID NO 131

```
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 131
ctccggatcc caaaccttca g                                              21

<210> SEQ ID NO 132
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 132
tgggatgaca atgacggaga ag                                             22

<210> SEQ ID NO 133
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 133
tgcgcttctt ttgttaattt gcag                                           24

<210> SEQ ID NO 134
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 134
cccgattttc ttgaagcttg ctc                                            23

<210> SEQ ID NO 135
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 135
acaacgactc aaagaagcag agaag                                          25

<210> SEQ ID NO 136
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 136
caacaacaaa ttggagagcc acag                                           24

<210> SEQ ID NO 137
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 137
```
tggaactcaa cgtggattgt gg                                              22

<210> SEQ ID NO 138
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 138
agttcaggcg tttgttgcat cc                                              22

<210> SEQ ID NO 139
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 139
atagctattc ctacaaggca ttttgc                                          26

<210> SEQ ID NO 140
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 140
tctctttgcg ttttggtatc ctg                                             23

<210> SEQ ID NO 141
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 141
ttcgaagaag aagaaagcag aaggag                                          26

<210> SEQ ID NO 142
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 142
ttatcgcggg ccaaaattaa cg                                              22

<210> SEQ ID NO 143
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 143
gcctgagtca actcggccat aag                                             23

<210> SEQ ID NO 144
<211> LENGTH: 22
<212> TYPE: DNA
<213> ORGANISM: Artificial sequence
<220> FEATURE:

<223> OTHER INFORMATION: Single strand DNA oligonucleotide

<400> SEQUENCE: 144
tacaacaagt ggagcgcgtg ag                                              22

<210> SEQ ID NO 145
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 145
tcaaccggaa aaggactgat ttc                                             23

<210> SEQ ID NO 146
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 146
gaaactaccc cataccgcat tcc                                             23

<210> SEQ ID NO 147
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 147
ggggtcctgt cttttgttc ttatc                                            25

<210> SEQ ID NO 148
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 148
tggtaaattc tgagcgtcca caac                                            24

<210> SEQ ID NO 149
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 149
ttggacctgt caagtgtcaa caatc                                           25

<210> SEQ ID NO 150
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 150
cgcgtaacgt agagagaatc tcaaac                                          26

<210> SEQ ID NO 151

```
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 151
tgaacctccg gctctttgag tc                                              22

<210> SEQ ID NO 152
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 152
ccccttcgtt ccaaacactt agc                                             23
```